(12) United States Patent
Garayt et al.

(10) Patent No.: US 7,393,980 B2
(45) Date of Patent: Jul. 1, 2008

(54) USE OF A COMPOSITION OF AN IONIC NATURE AS A SUBSTRATE REAGENT, A COMPOSITION CONSTITUTING A FLUORINATION REAGENT AND A METHOD USING SAME

(75) Inventors: Maxime Garayt, Charmes S/Rhone (FR); Virginie Le Boulaire, Bourg des Comptes (FR); Danielle Gree, Cesson-Sevigne (FR); René Gree, Cesson-Sevigne (FR); Vincent Schanen, Lyons (FR); Jean-Francis Spindler, Lyons (FR)

(73) Assignee: Rhodia Chimie, Aubervilliers (FR)

( * ) Notice: Subject to any disclaimer, the term of this patent is extended or adjusted under 35 U.S.C. 154(b) by 393 days.

(21) Appl. No.: 10/477,497

(22) PCT Filed: May 16, 2002

(86) PCT No.: PCT/FR02/01657

§ 371 (c)(1),
(2), (4) Date: Nov. 12, 2003

(87) PCT Pub. No.: WO02/092608

PCT Pub. Date: Nov. 21, 2002

(65) Prior Publication Data

US 2004/0144947 A1 Jul. 29, 2004

(30) Foreign Application Priority Data

May 17, 2001 (FR) .................................. 01 06531
May 15, 2002 (FR) .................................. 02 05984

(51) Int. Cl.
*C07F 9/02* (2006.01)

(52) U.S. Cl. .......................................... 568/9; 564/281

(58) Field of Classification Search ..................... 252/1; 564/281; 568/9
See application file for complete search history.

(56) References Cited

U.S. PATENT DOCUMENTS 4,978,769 A * 12/1990 Kysela et al. ............... 558/423

(Continued)

FOREIGN PATENT DOCUMENTS

FR  2 791 670  10/2000

(Continued)

OTHER PUBLICATIONS

Bhadury et al., A semi-molten mixture of hexadecyltributylphosphonium bromide and potassium fluoride in the synthesis of organofluorine compounds, Journal of Fluorine Chemistry 99 (1999) 115-117.*

(Continued)

*Primary Examiner*—Yvonne (Bonnie) Eyler
*Assistant Examiner*—Chukwuma O. Nwaonicha
(74) *Attorney, Agent, or Firm*—Buchanan, Ingersoll & Rooney, PC

(57) ABSTRACT

The invention relates to a novel method for producing nucleophilic substitutions, particularly of type SNAr and SN2. More specifically, the invention relates to the use as a fluorinating reaction medium of ionic liquid or fused salt comprising at least four carbon atoms. The invention can be used for the synthesis of fluoride derivatives.

33 Claims, 1 Drawing Sheet

U.S. PATENT DOCUMENTS 5,545,678 A * 8/1996 Giencke et al. ............. 523/404
5,545,768 A * 8/1996 Papenfhus et al. .......... 568/938

FOREIGN PATENT DOCUMENTS

| WO | WO 98 05610 | | 2/1998 |
|----|----|----|----|
| WO | WO 98/05610 | * | 2/1998 |
| WO | WO 00 37400 | | 6/2000 |
| WO | WO 01 87900 | | 11/2001 |

OTHER PUBLICATIONS

Bhadury et al., A semi-molten mixture of hexadecyltributylphosphonium bromide and potassium fluoride in the synthesis of organofluorine compounds, Journal of Fluorine Chemistry 99, 1999, 115-117.*

Bhadury, Pinaki S. et al.—Journal of Fluoride Chemistry (1999), 99(2), 115-117, XP004363094 the whole document.

Bhadury, Pinaki S. et al.—Journal of Fluoride Chemistry (1995), 73(2), 185-7, XP002244058, the whole document.

* cited by examiner

USE OF A COMPOSITION OF AN IONIC NATURE AS A SUBSTRATE REAGENT, A COMPOSITION CONSTITUTING A FLUORINATION REAGENT AND A METHOD USING SAME

This application is an application under 35 U.S.C. Section 371 of International Application Number PCT/02/01657 filed on May 16, 2002.

The present invention relates to the use of ionic compounds as a reaction medium or as a solvent in nucleophilic substitution reactions. It is directed more particularly to the preparation of fluoro derivatives or replacement of a leaving group, especially halogen or pseudohalogen, by a fluorine.

This substitution reaction is termed an aromatic nucleophilic substitution ($SN_{AR}$) when substitution takes place on an aromatic nucleus and is termed 2nd-order nucleophilic substitution ($SN_2$) when the substitution takes place on an aliphatic chain and when the kinetics are 2nd-order, i.e., the rate depends on the concentration both of substituting agents and of substrates.

One of the interesting aspects of the present invention is directed to improving aromatic nucleophilic substitution reactions referred to as Meisenheimer reactions.

It may be useful here to recall a few basic facts concerning Meisenheimer reactions.

Aromatic nucleophilic substitution reactions generally involve the following reaction scheme:

attack by a nucleophilic agent of an aromatic substrate with creation of a bond between said nucleophilic agent and said substrate, at a carbon carrying a leaving group, so as to form an intermediate compound, referred to as a Meisenheimer intermediate (when the nucleophile is an anion), or equivalent, then departure of said leaving group.

Given below are examples of $SN_{AR}$ intermediates, in which:

R represents the possible radicals;
n the number of substituent radicals;
EWG represents an Electron-Withdrawing Group;
lg represents a leaving group, or more particularly the leaving group in question.

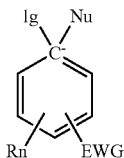

Example of a Meisenheimer intermediate, where Nu is an anionic nucleophile

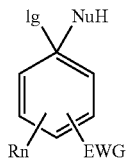

Example of a Meisenheimer intermediate equivalent, where NuH is a neutral nucleophile This type of reaction is particularly advantageous for obtaining halogenated aromatic derivatives and is used in particular to bring about exchanges between fluorine, on the one hand, and one or more higher-ranked halogens or pseudohalogens on an aromatic substrate, on the other hand.

The leaving group may therefore be a nitro group, advantageously a pseudohalogen, or preferably a halogen atom, above all with an atomic number greater than that of fluorine.

A pseudohalogen is understood to be a group whose departure leads to a chalcogenated anion, most frequently an oxygenated anion, with the anionic charge being carried by the chalcogen atom, and whose acidity is at least equal to that of acetic acid, advantageously to the second acidity of sulfuric acid and preferably to that of trifluoroacetic acid. In order to find a place on the acidity scale it is appropriate to refer to the pKas for medium to strong acidities ranging from carboxylic acids through to trifluoroacetic acid and to find a place on the Hammett constant scale (FIG. 1) starting from trifluoroacetic acid (constant of 1), or even the acidity scale given in the present specification.

To illustrate this type of pseudohalogens, mention may be made in particular of sulfinic and sulfonic acids perhalogenated on the sulfur-carrying carbon and of carboxylic acids perfluorinated a to the carboxyl function.

When the leaving group is a nitro group, it is generally replaced by a chlorine or fluorine atom. However, the majority of these reactants necessitate operations at very high temperatures and the mechanism does not always prove to be a nucleophilic substitution. Moreover, the departure of the nitro group leads to the formation of oxygenated and halogenated derivatives of nitrogen, which are particularly aggressive toward the substrate, or even explosive.

As far as the version is concerned which involves the substitution of a halogen atom present on an aromatic nucleus by another halogen atom, it generally necessitates at least one partial deactivation of said nucleus. For this purpose the aryl radical to be converted is preferably electron-poor and possesses an electron density no greater than that of benzene, closest to that of a chlorobenzene, preferably a dichlorobenzene.

This impoverishment may be due to the presence in the aromatic ring of a heteroatom (the impoverishment in this case involving a 6-membered ring), such as, for example in pyridine and in quinoline. In this particular case the impoverishment is sufficiently great that the substitution reaction is very easy and requires no particular auxiliary activation. The electron impoverishment may also be induced by electron-withdrawing substituents present on this aromatic ring. These substituents are preferably selected from groups which withdraw electrons by inductive effect or by mesomeric effect, as defined in the organic chemical reference work "Advanced Organic Chemistry" by M. J. March, 3rd edition, published by Willey, 1985 (cf. in particular pages 17 and 238). To illustrate these electron-withdrawing groups mention may be made in particular of the groups $NO_2$, quaternary ammoniums, Rf and in particular $CF_3$, CHO, CN, COY where Y may be a chlorine, bromine or fluorine atom or an alkyloxy group.

$SN_{Ar}$ reactions and especially those of halogen-halogen exchange set out above constitute in fact the principal synthesis pathway for obtaining fluorinated aromatic derivatives.

$SN_{Ar}$ reactions may also be of particular interest for making esters ($Nu^-$ is in this case in particular $Ac-S^-$ or $Ac-O^-$, with Ac being acyl [advantageously of 1 to 25 carbon atoms]), ethers ($Nu^-$ is in this case in particular $R-O^-$, with R being alkyl or aryl [advantageously of 1 to 25 carbon atoms]), thioethers ($Nu^-$ is in this case in particular $R-S^-$ with R being alkyl or aryl [advantageously of 1 to 25 carbon atoms]) and nitrites ($Nu^-$ is $CN^-$).

Accordingly, one of the most widely employed techniques for preparing a fluoro derivative consists in reacting a halogenated, generally chlorinated, aromatic derivative in order to exchange the halogen or halogens with one or more fluorines of mineral origin. Use is generally made of an alkali metal fluoride, most often of a high atomic weight, such as, for example, sodium fluoride and above all potassium, cesium and/or rubidium fluoride. Onium fluorides can also be used.

Generally speaking, the fluoride used is potassium fluoride, which constitutes a satisfactory economic compromise.

Under these conditions, many processes, such as, for example, those described in French addition certificate No. 2

353 516 and in the article Chem. Ind. (1978)-56 have been proposed and employed industrially in order to obtain aryl fluorides, aryls on which electron-withdrawing groups are grafted or else naturally electron-poor aryls, such as pyridine nuclei for example.

However, except where the substrate is particularly adapted to this type of synthesis, this technique has disadvantages, foremost among which are those which will be analyzed below.

The reaction is slow and, owing to a high residence time, requires substantial investment. This technique, as has already been mentioned, above all for the treatment of nuclei with a low level of electron impoverishment, is generally used at high temperatures, which can reach the regions of 250° C. or even 300° C., in other words the zone within which the most stable organic solvents begin to decompose.

The yields remain relatively mediocre, unless particularly expensive reagents are used, such as the fluorides of alkali metal whose atomic mass is greater than that of potassium.

Finally, in view of the price of these alkali metals, their industrial utilization is justifiable only for high added value products and when the improvement in yield and in kinetics justifies it, which is rarely the case.

In order to resolve or overcome these difficulties, numerous improvements have been proposed. Thus new catalysts are proposed, and mention may be made in particular of tetradialkylaminophosphonium compounds, and especially those described in patent applications filed in the name of the German company Hoechst and its successors Clariant and Aventis (for example, U.S. Pat. No. 6,114,589; U.S. Pat. No. 6,103,659; etc.) and in the patent applications filed in the name of the company Albemarle.

These new catalysts, admittedly, exhibit some advantages over the usual catalysts, but do not provide advantages in proportion with their price and their complexity.

Consequently one of the aims of the present invention is to provide reagents and operating conditions which allow substantial improvement of the kinetics of $SN_{Ar}$ reactions.

Another aim of the present invention is to provide reagents and to give operating conditions which allow in particular improved kinetics of $SN_{Ar}$ reactions even when the nucleus which is the venue of said $SN_{Ar}$ has only a low level of electron impoverishment.

Another aim of the present invention is to provide reaction media for nucleophilic substitution which allow improved solubility of ionic nucleophiles.

Another aim of the present invention is to provide reaction media for nucleophilic substitution which exhibit a high decomposition temperature, of at least 150° C., advantageously 200° C., and even 250° C.

Another aim of the present invention is to provide reaction media for nucleophilic substitution which allow good yields to be obtained without the need to go substantially beyond 200° C. for $SN_{Ar}$s on Ar—≡ in which the Ar is a phenyl for which the sum of the Hammett constants $\sigma_p$ of its substituents does not exceed 0.5.

Another aspect of the invention is to facilitate nucleophilic substitution reactions, particularly those considered to be 2nd-order nucleophilic substitutions.

The substantial problems of this type of reaction are well exemplified by those relating to exchange reactions between halogen and fluorine, since the aliphatic carbon in question comprises another substituent which withdraws electrons by inductive effect and/or is capable of constituting a leaving group.

The problem is exacerbated when the carbon comprises, in addition to the halogen or halogens to be exchanged, an atom or a group which is electron-withdrawing, particularly by inductive heat effect.

In particular, mention may be made of the exchange between fluorine and halogens, the halogen being carried by a halogen-bearing carbon which also carries:

at least one other halogen, or a radical connected to said carbon by a chalcogen;

or an aromatic;

or one or more of the above substituents.

The remarks below apply above all to chlorine-fluorine exchanges on substrates which carry polyhalogenated carbons, in general dichlorinated or polychlorinated carbons. This type of exchange may be considered as a paradigm (that is, a teaching by example) of the problems encountered in SN2 exchanges where the nucleophile is anionic, and of the solutions to said problems.

Fluorinated compounds are generally difficult to obtain. The reactivity of the fluorine is such that it is difficult if not impossible to obtain the fluorinated derivatives directly.

One of the techniques most widely employed to prepare the fluorinated derivative consists in reacting a halogenated derivative, generally a chlorinated derivative, to exchange the halogen with a mineral fluorine, generally an alkali metal fluoride, generally of high atomic weight.

Generally speaking the fluoride used is potassium fluoride, which constitutes a satisfactory economic compromise.

Except in cases where the substrate is particularly adapted to this type of synthesis, this technique has disadvantages, principal among which are those that will be analyzed below.

The reaction requires reactants such as alkali metal fluorides, for instance potassium fluoride, which are made relatively expensive owing to the specifications they are required to meet in order to be suitable for this type of synthesis: they must be very pure, dry and in an appropriate physical form, generally in atomized form.

Furthermore, this reaction does not work for a whole class of products, particularly those which carry on the halogen-bearing carbon (that is to say, the carbon which carries the halogen or halogens which it is intended to exchange with the fluorine).

Use is also made of reagents such as hydrofluoric acid, in liquid form or diluted with dipolar aprotic solvents. Hydrofluoric acid, however, is too powerful a reagent, and frequently leads to unwanted polymerization reactions or to tars.

In this case, and especially when the desire is for derivatives which are fluorinated on a carbon of alkyl (including aralkyl) type which is electron-poor owing to the presence of electron-withdrawing groups, the person skilled in the art is confronted with an alternative whose terms are hardly encouraging: either very harsh conditions are selected, and the products are mainly tars, or the reaction conditions are mild, and in the best-case scenario the substrate recovered is unchanged. Finally, it should be pointed out that certain authors have proposed carrying out exchanges by using salts of hydrofluoric acid as reagent in the presence of heavy elements, especially in the form of mineral cations (in the present description, heavy elements are considered as being the transition elements and the elements of groups IIIB, IVB and VB which belong to periods greater than the third), in oxide or fluoride form. Among the heavy elements used it is appropriate to mention arsenic, antimony and heavy metals such as silver or quick-silver (mercury).

Another problem lies in the selectivity of the reaction: when there are two or more halogens to be exchanged on a single sp³ carbon it is often difficult to exchange only some of them.

Another aim of the present invention, accordingly, is to provide a process which is capable of effecting the exchange between, on the one hand, heavy halogens such as chlorine and, on the other hand, fluorine by significantly improving the specificity of the reaction.

Another aim of the present invention is to provide a process which is capable of effecting exchange between, on the one hand, heavy halogens such as chlorine, and on the other hand, fluorine, using mild reaction conditions.

Another aim of the present invention is to provide a process which makes it possible to use a source of fluorine whose morphology is relatively uncritical.

Another aim of the present invention is to provide a process which allows only one halogen atom (in particular chlorine) to be exchanged out of two (in particular two chlorines) or out of three possible atoms (in particular three chlorines).

Another aim of the present invention is to provide a process which allows only two halogen atoms out of three possible atoms to be exchanged.

Another aim of the present invention is to provide a process which, on a single sp³ carbon, allows only one halogen atom (in particular chlorine) to be exchanged out of two (in particular two chlorines) or out of three possible atoms (in particular three chlorines).

Another aim of the present invention is to provide a process which, on a single sp³ carbon, allows only two halogen atoms out of three possible atoms to be exchanged.

Another aim of the present invention is to provide a process which allows the molecules or atoms to be exchanged only insofar as to do so makes it possible to obtain carbon atoms which carry only one fluorine atom together with one or two other, non-fluorine halogens.

Another aim of the present invention is to provide a process which allows the molecules or atoms to be exchanged only insofar as to do so makes it possible to obtain carbon atoms which carry only two fluorine atoms together with one other, non-fluorine halogen.

Another aim of the present invention is to provide a process which avoids the use of a high quantity of metals considered expensive or toxic such as mercury and/or silver.

Another aim of the present invention is to provide a process which makes it possible to reduce the amounts of heavy elements, particularly those considered expensive or toxic, such as mercury and/or silver, such that the molar ratio between the metal and the substrate whose halogen atoms are to be exchanged is not more than 0.5, advantageously than 0.2, and preferably then 0.1.

Another aim of the present invention is to provide a process which completely avoids the use of elements, and particularly of heavy metals, which in particular are considered expensive or toxic, such as mercury and/or silver, such that none of the abovementioned elements is added to the reaction mixture; in other words, that the concentrations of each of said metals do not exceed values of $10^{-3}$ M; advantageously $10^{-4}$ M, preferably $10^{-5}$ M.

More generally the present invention aims to carry out nucleophilic substitution reactions, especially aromatic nucleophilic substitution and/or 2nd-order nucleophilic substitution reactions, which allow the reaction to be carried out with relatively weak nucleophiles.

Another aim of the present invention is to provide a technique which allows a nucleophilic substitution reaction to be carried out with neutral or anionic nucleophiles whose associated acid has a pKa of not more than 5, preferably not more than 4, said pKa being measured in aqueous phase.

Another aim of the present invention is to provide a process which enables an $SN_{Ar}$ or $SN_2$ reaction to be carried out that allows a halogen heavier than fluorine to be replaced by fluorine.

Another aim of the present invention is to provide a process which allows the replacement of a pseudohalogen by a fluorine.

Another aim of the present invention is to provide a process which allows chlorine-fluorine exchange to be carried out on an aliphatic atom (i.e., one with sp³ hybridization) which carries at least one other, heavier-than-fluorine halogen to be exchanged with the fluorine.

In particular, another aim of the present invention is to provide a process which allows halogen-fluorine, and especially chlorine-fluorine, exchange to be carried out on a substrate or the halogen is carried by a halogen-bearing carbon which likewise carries:

at least one other halogen, or a radical connected to said carbon by a chalcogen;

or an aromatic;

or one or more of the above substituents.

These aims and others which will appear subsequently are achieved by means of a reaction medium comprising an ionic compound whose cation is of general formula G:

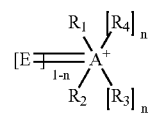

where $R_1$, $R_2$, $R_3$, and $R_4$, which are identical or different, are selected from monovalent hydrocarbon radicals;

where n is selected from zero and one;

where A is a semimetal atom from group VB (nitrogen group) (the periodic classification of the elements which is used in the present specification is that of the supplement to Bulletin de la Société Chimique de France, January 1966, No. 1);

where E is a divalent group which carries at least one double bond conjugated with the E=A double bond and/or carries another semimetal atom which carries at least one doublet which is conjugated directly or indirectly with the E=A double bond, advantageously a semimetal of group VB whose doublet is conjugated directly or indirectly with the double bond E=A.

DETAILED DESCRIPTION

Figure 1:
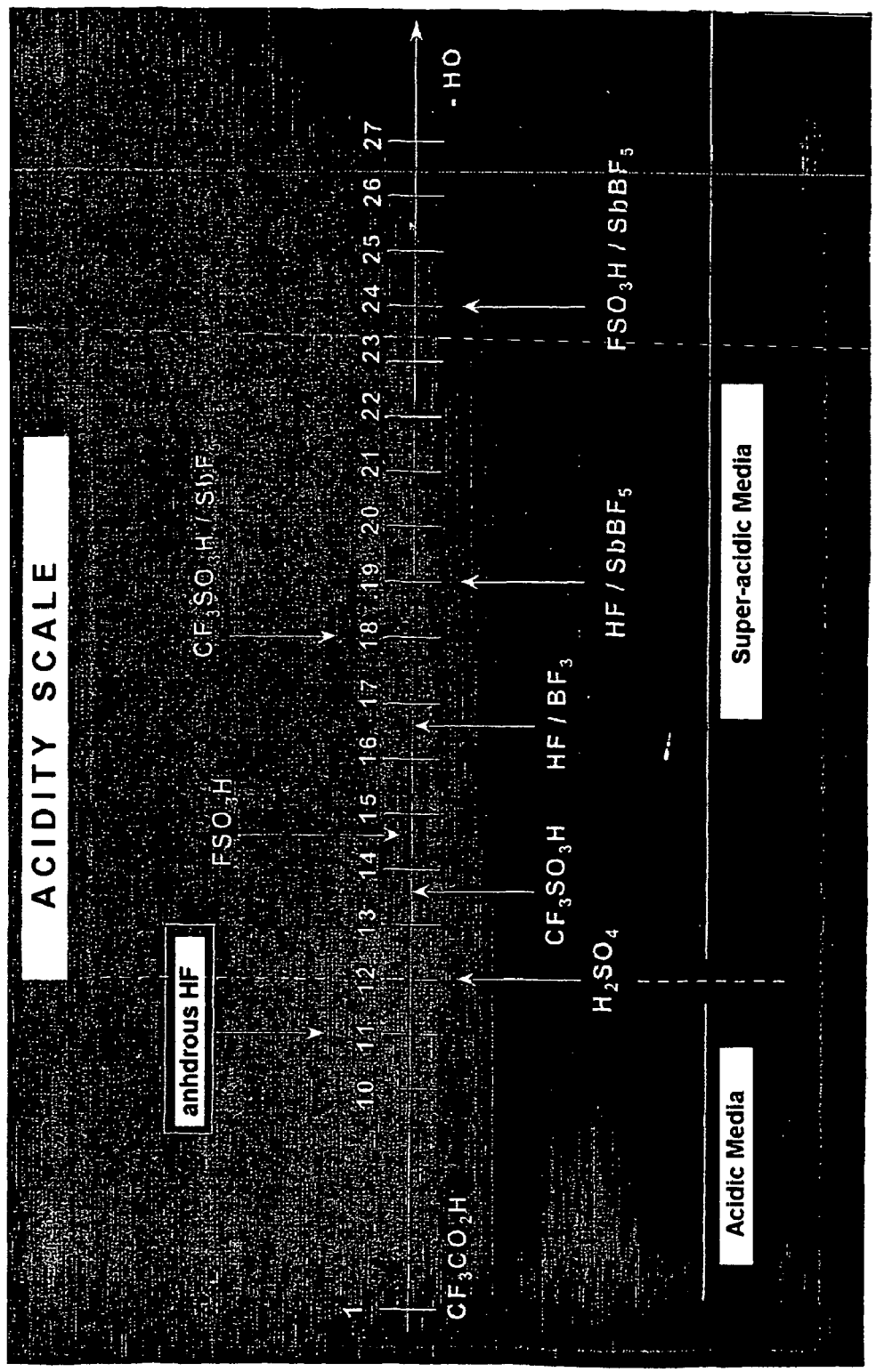
FIG. 1 is a representation of the Hammett constant scale.

According to one embodiment of the present invention, n is 1, which means that A in this case is advantageously phosphorus. And, therefore, that the compound of general formula G is very preferably a phosphonium compound. In this case the most advantageous results are obtained for $SN_{Ar}$s.

Where n is zero, the composition constituting a reagent or a reaction medium is more polyvalent but its advantage is manifested above all for the synthesis of aliphatic fluoro derivatives from substrates which carry an sp³ halogen-bearing carbon which itself carries a radical or a group which is electron-withdrawing, with a Hammett constant σp of at least 0.1.

The invention (with n being zero or 1) is advantageous for $SN_{Ar}s$ with one of the aforementioned leaving groups and with anionic nucleophiles, especially those mentioned above. It is particularly advantageous with one or more halogens or pseudohalogens as leaving group. Halogens, and especially chlorine, are preferred as leaving groups. The replacement of at least one halogen heavier than fluorine, and in particular of at least one chlorine, is a particular object of the present invention. The preferred concepts and values of the aryls and alkyls are the same in both versions.

According to the present invention it is advantageous to select cations and amounts of cations such that the cation concentration in accordance with the formula G is at least 2 moles per liter or more exactly two cation equivalents per liter, preferably 3 equivalents and 4 equivalents per liter. The higher this concentration the better the yields, but not necessarily the selectivity.

For compounds of formula G where n is zero it is desirable for the molecular mass of the cation to be not more than 300, advantageously than 250, more preferably than 200. When the cations are polyvalent (that is, carry two or more positive charges), these values must be taken per unit charge; in other words, it will be possible for a divalent cation to have a molecular mass of more than twice the above-mentioned masses.

In order to prevent excessive crystallinity and to lower the melting point, it is preferable for the compounds of formula G according to the invention to have a molecular mass of at least 100.

It is preferable for the reaction medium made up primarily of the ionic solvent to be as dry as possible. However, owing to the high hygroscopicity of the cations according to the present invention, it is appropriate to ensure that these reaction media are dehydrated prior to use. The reaction medium prior to use is advantageously such that the ratio by mass between the salt whose cation corresponds to the formula G and water is not more than 200 ppm, preferably than 100 ppm (in this ratio, the numerator is constituted by the water, of course). One effective means of dehydrating consists in heating under vacuum for 2 h, preferably for 8 h under vacuum at 70° C., the vacuum being the vacuum of the slide vane rotary piston pump, or $10^{-2}$ mm of mercury.

Said reaction medium is advantageously aprotic and anhydrous. In particular it is desirable anhydrous is such that the strongest acid present in the medium, not taking into account the substrate, has a pKa of at least.

The protons obtained from acid(s) whose pKa is less than 20, advantageously than 25, preferably than 30, are considered "labile hydrogens".

The more aprotic the medium, i.e., the lower the amount therein of releasable protons in the reagent, the lower the risk of side reaction and the better the yield.

Thus it is preferable, in the composition according to the present invention, serving as reagent or as reaction medium, for the amount of labile hydrogen atoms to be such that the ratio between the amount, in equivalents, of labile hydrogen (numerator) and the amount of cation of formula G, expressed in equivalents, is not more than 1%, advantageously than 1 per thousand, preferably than 1000 ppm (in moles, or equivalents when the species in question are polyfunctional).

Referring to the version where n is 1, the ionic compounds according to the present invention are advantageously at least one phosphonium salt containing at least 4 carbon atoms. Thus use is made as reaction medium in a nucleophilic substitution reaction, advantageously an aromatic nucleophilic substitution reaction, of at least one (quaternary) phosphonium salt containing at least a carbon atoms.

The medium according to the present invention can be considered to be a melted organic salt, a salt which can include a proportion of a compound known as a polar solvent. However, the presence of such solvents has a tendency to lower the beneficial effect of said medium.

Indeed, in the course of the research which led to the present invention, it has been found that, at low concentration, the effect of said phosphonium compounds is limited to that of a phase transfer agent, and that as soon as the concentration increases, and the moment is reached at which the phosphonium ceases to be a simple phase transfer agent and becomes the dominant element by mass (not taking into account the substrates, reagents or converted substrate), the nature of its effect changes and leads to degrees and kinetics of conversion which cannot be reduced to the simple effect of an increase in the concentration.

It is therefore desirable for said reaction medium to have a mass ratio between the sum of the polar solvents and the sum of the phosphonium salts ([S.P.]/[P⁺]) of not more than 1, advantageously than 1/2, preferably than 1/5.

Said phosphonium compound advantageously corresponds to the formula (I):

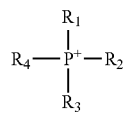

where $R_1$, $R_2$, $R_3$ and $R_4$, which are identical or different, are selected from hydrocarbon radicals and can be connected to one another.

According to one preferred embodiment of the present invention the phosphonium compound or compounds which constitute(s) the medium according to the present invention is or are such that said hydrocarbon radicals $R_1$, $R_2$, $R_3$ and $R_4$ are selected from those of the list below, which is given in order of preference:

1. alkyls,
2. optionally substituted aryls,
3. amino and imino groups, advantageously those whose nitrogen attached to a P does not carry hydrogen,
4. hydrocarbyloxy radicals.

It is advisable for at least one of the carbon chains carried by the phosphonium to be of alkyl type and hence aliphatic in nature; that is, for the carbon providing the link with the phosphorus atom to be of $sp^3$ hybridization.

The reason for this—and this is one of the surprising teachings—is, on the one hand, that the greater the aliphatic nature of the phosphonium compounds the better the result; on the other hand, under the conditions of use, the phosphonium compounds, despite having the reputation of being unstable and giving rise spontaneously to alkenes by compositions, have been found to be very stable. It is nevertheless doubtless appropriate, when the aim is to use very harsh conditions (at least 250° C. and even 200° C.; especially if the anion is relatively basic [pKa of the associated acid greater than 2]), to avoid bonds where the phosphorus carries tertiary or even secondary carbons which themselves carry a removable hydrogen in beta position.

It follows that it is desirable for at least two, advantageously three, of the carbon chains carried by the phosphonium to be aliphatic in nature, and even for the four carbon chains carried by the phosphonium to be aliphatic in nature.

In order to constitute a medium which is highly suitable for nucleophilic substitutions, particularly those of $SN_{Ar}$ type, the total carbon number of the phosphonium compounds of formula I is not more than 50, advantageously than 35, preferably than 25. In the case of a mixture of phosphonium compounds it is necessary to think in terms of average carbon number relative to the phosphorus atom number. In this case the carbon atom number may become fractional.

For aliphatic phosphonium compounds it is preferable to limit still further the molecular mass of the phosphonium compound or compounds. Accordingly, when it (they) is (are) at least partially aliphatic, the phosphonium compound(s) of formula I has (have) a total carbon number of not more than 30, advantageously than 25, preferably than 20.

This preference can also be expressed by indicating that the average mass of the substituents of the phosphonium compound or compounds does not exceed, preferably, 700 per phosphorus atom in phosphonium form, advantageously 500. The minimum advisable value is 56, advantageously 80, preferably 100.

More precisely, when at least two and advantageously three of the carbon chains carried by the phosphonium are aliphatic in nature, the quasi optimal total carbon number is established at values of not more than 25, preferably than 20.

The term alkyl is taken in its etymological sense of the residue of an alcohol from which the OH function has been removed. It therefore embraces, in particular, radicals whose free bond is carried by an $sp^3$ hybridized carbon atom, said carbon atom being connected only to carbons or hydrogens. In the context of the present invention, among alkyls, it is appropriate to mention, in addition to the radicals of formula $C_nH_{2n+1}$, those derived therefrom by substitution by atoms and/or functional groups (in accordance with the applications it is preferable, in order to avoid side reactions, to select functional groups which are inert under the conditions in which the invention is implemented) and especially those which carry one or more ether functions, and in particular the mono-, oligo- or poly-ethoxy chain sequences obtained from alkene epoxide(s), especially ethylene epoxide.

Said alkyls may also carry quaternary ammonium or phosphonium functions; in that case, the phosphonium compounds are polycationic. Although not excluded, they are not among the preferred compounds.

The $R_1$, $R_2$, $R_3$ and $R_4$ radicals advantageously have not more than 20 carbon atoms and in total not more than 50 carbon atoms.

For reasons of ease of synthesis it is preferable for at least three of $R_1$, $R_2$, $R_3$ and $R_4$ to be identical.

Subject to the constraints of ring strain, the $R_1$, $R_2$, $R_3$ and $R_4$ radicals may be connected to one another and form rings, although this does not constitute the most preferred compounds; they may also form rings with another phosphonium compound, for example, the compounds resulting from the quaternarization of diphosphabicylcooctane.

$R_1$, $R_2$, and $R_3$ may be connected to one another and form rings.

In neutral form the phosphonium salt corresponds advantageously to the formula (II);

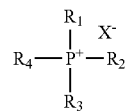

where $X^-$ represents an anion (or a mixture of anions) which ensures electroneutrality; advantageously the anion or anions $X^-$ represent(s) a singly charged anion.

According to one preferred embodiment of the present invention, $X^-$ is an anion such that XH is at least as acidic as acetic acid, advantageously as the second acidity of sulfuric acid.

These counterions are advantageously selected from relatively normucleophilic anions and anion mixtures $X^-$; that is, when they are single, are such that XH has a pKa of not more than 3, advantageously than 2, preferably—than 1, more preferably than zero, and, when they consist of a mixture of anions, at least one of the anions is relatively nonnucleophilic. Thus, in accordance with one preferred embodiment of the present invention $X^-$ is selected such that $X^-$ is at most as nucleophilic as the nucleophile, advantageously less so, and even significantly less so (in other words, such that the pKa of XH is less by 1, advantageously by 2, preferably by 3, than the pKa of the acid associated with the nucleophile).

According to another preferred embodiment of the present invention, when the nucleophile is anionic, $X^-$ or one of the anions which it represents is the nucleophile or one of the nucleophiles of said nucleophilic substitution.

$X^-$ is selected from halogens, pseudohalogens and mixtures of these halogens or pseudohalogens, advantageously halogens from periods greater than that of fluorine (except when fluoride is the soluble nucleophile) and mixtures of halides.

In accordance with the present invention it has been shown that bromides and chlorides are preferred co-anions $X^-$; in particular it is advisable to ensure that the sum of the bromide ions and chloride ions is at least equal to ½ times, advantageously to ¾ times, the amount of cation of formula G (expressed in equivalents).

The chloride is preferred for the $SN_{Ar}s$; it is also advantageous for the chloride ions to be in an amount at least equal to 1/2 times, advantageously to 3/4 times, the amount of cation of formula G (expressed in equivalents).

Another aim of the present invention is to provide a composition which can be used as a reactant for implementing the use described above.

This aim, and others which will emerge subsequently, is achieved by means of a composition useful as a nucleophilic substitution reagent, comprising apart from the substrate, in a liquid phase for successive or simultaneous addition:
(a) at least one compound of formula G, advantageously a quaternary phosphonium compound or a mixture of quaternary phosphonium compounds, containing at least 4 carbon atoms,
(b) a co-anion,
(c) a nucleophilic substituent, optionally in salt form,
(d) further components,
wherein, when (d) comprises an optional polar solvent, the latter is present in an amount such that the ratio by mass between the sum of the polar solvents and the sum of the salts of compound(s) of formula G, advantageously of phosphonium compound(s) ([S.P.]/[P$^+$]), i.e., [S.P.]/(a+b), is not more than 1/, advantageously than 1/3 , preferably than 1/4, more preferably than 1/5, and in that the sum of (a)+(b)+(c)+(d) represents 100% of said liquid phase.

The amount of the further components assembled under (d) is advantageously low. Thus it is desirable that, apart from substrate, the mass ratio between component (d), on the one hand, and components (a)+(b)+(c), on the other hand, is not more than 1, advantageously than 1/2, preferably than 1/3.

According to one preferred embodiment of the present invention, when the nucleophile is ionic, at least part of the co-anion is formed by said nucleophile; in other words, the sum of the anions (expressed in equivalents, of course) other than the nucleophile is less than the amount of compound(s) of formula G, advantageously of phosphonium compound(s) and of countercation(s) (expressed in equivalents, of course) of said nucleophile, advantageously less than the amount of compound(s) of formula G, advantageously of phosphonium compound(s) on its (their) own.

When the nucleophile is ionic (i.e., in salt form) the molar ratio between the cation(s) [i.e., the cations forming counterions of an anionic nucleophile] of component (c), expressed in terms of equivalents, and component (a), expressed in terms of equivalents of compound(s) of formula G, advantageously phosphonium compound(s), is greater than 0.01, advantageously than 0.02. As in this case the effect of the compound of formula G, advantageously of the phosphonium compound, on the liquid phase is less, it is desirable for the upper value of said ratio not to exceed 2/3, advantageously 1/2, preferably 1/3.

When the nucleophile is anionic, it may be advantageous to use the nucleophile both as co-anion of the compound(s) of formula G, advantageously of the phosphonium compounds, which ensure electroneutrality, and as nucleophile; in this case, the molar ratio (or equivalents ratio when the components are polyfunctional) between component (c), expressed in monovalent anion equivalents, and component (a), expressed as equivalents of compound(s) of formula G, advantageously of phosphonium compound(s), is at least 0.5; advantageously at least 0.6, preferably at least 0.7.

Said composition may further comprise one (or more) solid phase(s) in kinetic or thermodynamic equilibrium with the above liquid phase.

Generally said solid phase or said solid phases comprise(s) at least one salt formed from a mineral cation and from the anion corresponding to said nucleophile and/or to the leaving group of said nucleophilic substitution.

When said nucleophilic substituent is present, at least partly, in the liquid phase in the form of a salt with a mineral cation, the molar ratio (or equivalents ratio) between said mineral cation (MC) in dissolved form and component (a) ([MC]/P⁺]) is advantageously at least 1/100, preferably at least 1/20, more preferably at least 1/10.

The use of solid phase(s) is very useful when the exchange is between fluoride (nucleophile) and chlorine (leaving group). In this case the nucleophile is the fluoride ion, which is advantageously in the form of an alkali metal salt; generally potassium salt or cesium salt.

With reference to the embodiment when n is zero, a family of ionic compounds is obtained some of which are qualified for use as ionic solvents (generally when the melting point of the salt is not more than 100° C.

These ionic compounds whose cation has just been detailed are in some cases already known to the person skilled in the art. Thus mention may be made of the article from Journal of Fluorine Chemistry (1999) 1-3. Reference may also be made to the review published in Angewandde Chemie entitled Ionic Liquids—"New Solution for Transition Metal Catalysis" by Peter Wasserscheid and Wielm Keim: Angew. Chem. Int. Int. Ed., 2000, 39, 3772-3789.

According to the present invention the co-anion or co-anions are advantageously selected:
  from anionic nucleophiles (which play the part of nucleophile in the nucleophilic substitution),
  from anions, advantageously monovalent anions, for which the associated acid has an acidity at least equal to that of trifluoroacetic acid, and
  from mixtures of anionic nucleophiles and anions, advantageously monovalent anions, for which the association acid has an acidity at least equal to that of trifluoroacetic acid.

In the course of the study which led to the present invention it was found that these ionic liquids, when they were used under the same conditions (in other words within the same ranges in particular of time, temperature, pressure and absence of water) as those of the customary solvents, made it possible to be at least as efficient as the customary solvents and that, under certain conditions, they made it possible to obtain particularly advantageous results.

Besides the fact that they make it possible to carry out reactions which in ordinary time are very difficult to carry out in nonionic solvents, these ionic solvents, or melted salts, also allow the selectivity of the exchange with extremely high selectivity coefficients. As can be seen below it is possible to vary the lipophilicity and the molecular mass of the cation in order to promote certain reactions over others.

Moreover, surprisingly, in the chlorine-fluorine exchange, the preferred co-anions are not those which are usually preferred.

In particular, the anions which give the best results in the two exchanges are neither complex anions nor anions having a very widely delocalized charge. Thus anions of the type $PF_6^-$, $BF_4^-$, triflic and triflimide anions, although giving good results, are not those which give the best.

The preferred anions are halide anions, without it being possible to give any entirely satisfactory mechanistic explanation.

Although phosphonium compounds in which n is zero give results which are particularly advantageous for reactions of type $SN_{Ar}$ with an actual or supposed Meisenheimer intermediate, the other cations, especially those when n is zero, are more polyvalent, and have the advantage of being liquid at a lower temperature, at least in general.

When n is zero the compound of formula G is advantageously such that A is nitrogen; although it is possible for it to be phosphorus, this limits the use of the media, owing to oxidizability of these compounds and their relative instability.

When n is zero, it is desirable for the divalent radical E to be such that E represents an equal radical D-A" to form a compound of formula (IIa):

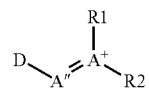

where A" is an atom from group VB or else a carbon atom which carries hydrogen or is substituted by a hydrocarbon radical $R_5$,
where the radical D is selected from
  chalcogens singly substituted by a monovalent $R_6$ radical (in which case the chalcogen constitutes said doublet-carrying semimetal), semimetals from group VB, especially nitrogen or phosphorus (in which case the semimetal from group V constitutes said doublet-carrying semimetal), preferably nitrogen;
either monosubstituted by a functional group or a divalent radical $R_7$, to form a radical D of formula $-A'=R_7$;
or by two monovalent hydrocarbon radicals, $R_6$ and $R'_6$, to form a radical D of formula $-A'(R_6)(R'_6)$ and
sp²-hybridized carbon atoms substituted by a functional group or a divalent radical $R_7$ which carry a hydrogen or are optionally substituted by a carbon radical $R_6$.

It ought to be recalled that, in this formula, when n is zero, the semimetals from group VB are preferably a nitrogen, whether for A" or for A'.

When A" is an atom from group VB, and in particular a nitrogen, it is preferred for D to be selected from sp² carbon atoms substituted by a functional group or by a divalent radical $R_7$ which carries a hydrogen or is optionally substituted by a carbon radical $R_6$, to give a formula of D specified below. When said carbon carries a hydrogen, that hydrogen occurs in place of $R_6$

As stated before, it is desirable for the cation of formula G in which n is zero to comprise a semimetal atom (which is saturated, i.e., does not carry a double bond), featuring resonance with a π bond connecting two atoms of which at least one is a disubstituted, positively charged atom from group VB; advantageously an organic cation comprising a trivalent atom from group VB (nitrogen group in Mendeleev's table), advantageously nitrogen, the doublet of which atom is conjugated directly or indirectly to a π bond which connects two atoms of which at least one is an atom from group VB (namely A)°.

The semimetal atoms exhibiting a resonance (directly or indirectly via one or more double bonds, advantageously carbon-carbon bonds) with a bond, generally a doublet conjugated with a π bond, are advantageously selected from those which have a strong mesomeric donor effect, in other words those which, together with their possible substituents, have a significantly negative R factor (resonance contribution; see in particular "March" 3rd edition, table 6 on page 248), more specifically an R factor of not more than –0.4, advantageously not more than –0.6; preferably not more than –1.5; more preferably not more than –2. When there are two or more semimetal atoms which have the above resonance properties, it is then possible to add up said R factors, said sum in that case being advantageously not more than –0.5, preferably than –0.8, more preferably not more than –2.

Said organic cation containing a saturated semimetal atom exhibiting resonance with a π bond is advantageously such that said semimetal atom is a chalcogen substituted by an aromatic or aliphatic radical, or preferably a trivalent atom from group VB, which is preferably a trisubstituted atom which forms a tertiary base. Said organic cation may contain two or more saturated semimetal atoms which exhibit resonance with said π bond. This has the advantage of better delocalization of the positive charge.

According to one particularly advantageous embodiment of the present invention said π bond connecting two atoms is the π bond of an iminium function ($>C=N^{\pm}<$).

The iminium function can be written as follows.

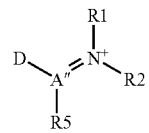

where A" represents a carbon
where D is selected from:
chalcogens monosubstituted by a monovalent radical $R_6$,
a semimetal from group VB, especially nitrogen or phosphorus, preferably nitrogen;
either monosubstituted by a functional group or a divalent radical $R_7$:

or by two monovalent radicals R6 and R'6; and
sp² carbon atoms substituted by a functional group or a divalent radical $R_7$ which carry a hydrogen where optionally substituted by a carbon radical $R_6$.
where $R_5$ is selected from hydrogen, the values of D and from hydrocarbon radicals, advantageously aryls and above all alkyls.

It is preferable for the radical D and its iminium function to be arranged such that the nitrogen atoms and the atoms of said semimetal are as far apart as possible; in other words, and for example, such that the nitrogen of the iminium function is that one of the two atoms connected by the π bond which is furthest from the trivalent atom from group V. What has just been said with regard to the iminium function is generally valid for all atoms from group VB which are connected by the π bond, where the π bond contains a carbon atom and an atom from group V.

According to the present invention it is preferred for the organic cation containing a trivalent atom from group VB whose doublet is conjugated to a π bond to have a chain sequence, or rather a skeleton, of formula $>N—[C=C]_v—C=N^{\pm}<$, where v is zero or is an integer selected from the closed range (that is, the range including the end points) from 1 to 4, advantageously from 1 to 3, preferably from 1 to 2. The above chain sequence corresponds preferably to the formula $$Q-[C(R_8)=C(R_6)]_v C(R_5)=N(R_1)(R_2)$$

where Q represents
a chalcogen substituted by an aliphatic or aromatic radical $R_9$; or
more preferably a nitrogen disubstituted by two identical or different aliphatic or aromatic radicals $R_9$ and $R_{10}$: $(R_{10})(R_9)N—$;
where v is zero or is an integer selected from the closed range (that is to say, the range including the end points) from 1 to 4, advantageously from 1 to 3, preferably from 1 to 2 and where $R_1$, $R_2$, $R_3$, which are identical or different, are selected from hydrocarbon derivatives, advantageously alkyl derivatives, of not more than 4 carbon atoms and hydrogen.

Advantageously, according to the present invention, said trivalent atom from group VB forms or constitutes a tertiary amine.

More specifically it is desirable for said organic base containing a trivalent atom from group VB whose doublet is conjugated to a π bond to constitute a molecule of the following formula:

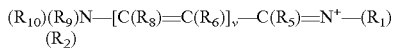

where v is zero or an integer selected from the closed range (that is to say, the range including the end points) from 1 to 4, advantageously from 1 to 3, preferably from 1 to 2 and where $R_1$, $R_2$, $R_5$, $R_6$ and $R_8$, which are identical or different, are selected from hydrocarbon groups, advantageously alkyl groups of not more than 4 carbon atoms and hydrogen and where $R_{10}$ and $R_9$, which are identical or different, are selected from hydrocarbon groups, advantageously alkyl groups of not more than 4 carbon atoms, it being possible for one or two of the substituents $R_1$, $R_2$, $R_5$, $R_8$, $R_9$ and $R_{10}$ to be connected to other remaining substituent(s) to form one or two or more rings, especially aromatic rings; see below.

The delocalization effect is particularly marked when said π bond connecting two atoms is intracyclic (or a mesomeric form is intracyclic), especially when it is intracyclic in an aromatic ring.

This is particularly the case with pyridine rings, diazine rings (preferably meta-diazine rings; see formulae below) and rings which are derived therefrom, such as quinoline or isoquinoline, such as for example [in the formulae given below the three positions of the rings may be substituted, but the substituents (alkyls or aryls, and their carbon number of course forms part of the count of the total number of carbons) neither have been featured nor are even desirable]:

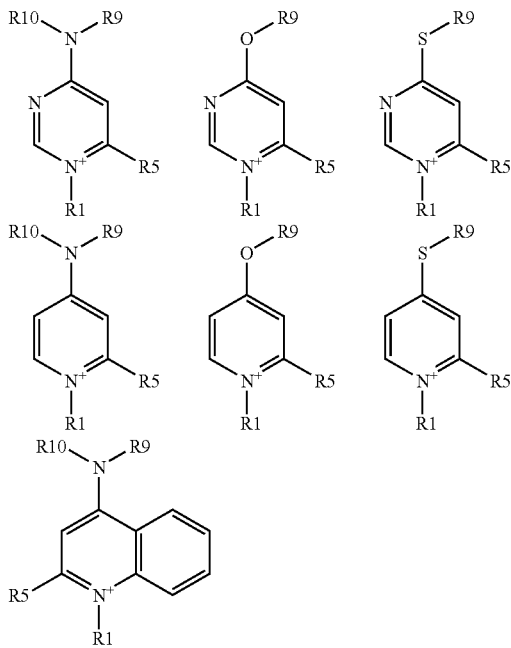

Accordingly the pyridine rings, especially those enriched by the presence of one or more semimetal atoms, particularly when the sum of the R factors (see above) is not more than −1.5, advantageously than −2, constitute particularly satisfactory cations.

More specifically, the organic base which contains a saturated semimetal atom exhibiting resonance with a π bond may advantageously be selected from the dialkylaminopyridiniums, particularly in para or ortho position (i.e., in position 2 of the pyridine or 4; see formula above); DBU (diazabicycloundecene) also gives an advantageous cation.

The 5-membered rings are particularly advantageous when they possess two or three heteroatoms.

For example, the structures of the imidazole, oxazole or cyclic guanidine type, or even of the indole type

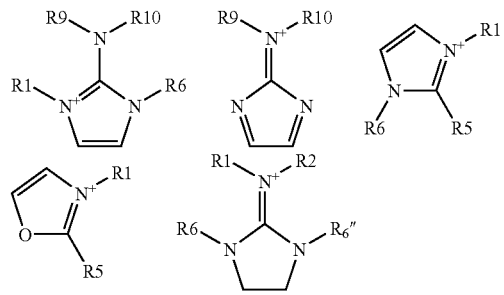

$R_6'$ and $R_6''$ have the same value as $R_6$.

It is possible for the free aryl positions (forming part of an aromatic) or aliphatic positions (whose attachment point is an $sp^3$ carbon) to be substituted. However, this presents no great advantage and has the drawback of making the cation heavier.

The triazole structures can also be envisaged

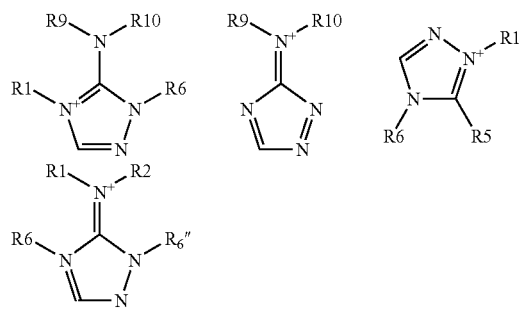

The pyrazole structures are also possible, but less satisfactory owing to the lower resonance.

It should also be mentioned that, among non cyclic structures, there may be a certain advantage in using guanidinium structures, which have the feature of being easily derived from guanidine and of presenting a highly resonant formula

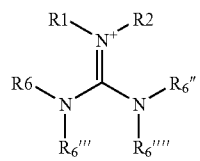

where $R_6'''$ and $R_6''''$ are selected from the same values as $R_6$; they may be identical or different from the other radicals $R_6$, and from the $R_1$ and $R_2$ radicals. It is preferable, if the desire is for compounds having a low melting point, for the molecule to be asymmetrical.

$R_6'''$ and $R_6''''$ can be connected to one another to form rings, advantageously aromatic rings.

It is advantageous, especially when the cation has less than 7 carbon atoms in its structure, to avoid any symmetry, which is capable of facilitating crystallization. Accordingly, the substituents of the nitrogens (more generally of the atoms A and A', or even A") are preferably different in size.

The radicals $R_1$ to $R_{10}$ are selected such that none of the atoms from the nitrogen group and none of the chalcogens carries a hydrogen, subject to the following proviso: the radicals $R_1$ to $R_{10}$, which can independently be identical or different, are advantageously selected from alkyls and aryls. Furthermore, $R_5$ and $R_8$ can be aryloxy groups, alkyloxy groups, amino groups substituted by two alkyls, by two aryls or by one alkyl and one aryl. $R_6$, when carried by a carbon, may also be a dimethylamino, an aryloxy or an alkyloxy.

Thus $R_5$ may be selected from hydrogen, the values of D and from hydrocarbon radicals, advantageously aryls and especially alkyls.

Subject to the proviso that they are not carried by a chalcogen or an atom from group VB, they may also be hydrogen like $R_5$, $R_6$ and $R_8$.

The total number of carbons when n is zero in the formula G is advantageously not more than 30, preferably not more than 20, more preferably not more than 15. It is desirable for not more than two, and even preferable for not more than a single one, of the hydrocarbon groups, when they are such, $R_1$, $R_2$, $R_5$, $R_6$, $R_8$, $R_9$ and $R_{10}$ to have a number of carbons greater than 6.

In order to facilitate the treatment of the reaction mixtures it is preferable for the cation of formula G to be stable in the presence of water and to be immiscible therein in any proportion.

The term alkyl is taken in its etymological sense of the residue of an alcohol from which the OH function has been removed. It therefore embraces, in particular, radicals whose free bond is carried by an $sp^3$ hybridized carbon atom, said carbon atom being connected only to carbons or hydrogens. In the context of the present invention, among alkyls, it is appropriate to mention, in addition to the radicals of formula $C_nH_{2n+1}$, those derived therefrom by substitution by atoms and/or functional groups (it is preferable to avoid side reactions by selecting functional groups which are inert under the conditions in which the invention is implemented) and especially those which carry one or more ether functions, and in particular the mono-, oligo- or poly-ethoxy chain sequences obtained from alkene epoxides, especially ethylene epoxide. Finally, as has been seen above, the radicals $R_1$ to $R_{10}$ may be connected to one another to form rings, and especially aromatic heterocycles.

Imidazoliniums give particularly advantageous results, particularly with regard to chlorine, fluorine exchanges on sp hybridized carbons. Imidazoliniums which have given the best results are those in which $R_5$ is a hydrogen and in which $R_1$ and $R_6$ are alkyl while not having the same chain length. The preferred and most active chain lengths are those such that when $R_1$ is methyl and $R_6$ is between methyl and butyl. The experiments in which the chain length of $R_6$ is 8 carbon atoms are less efficient but display a high selectivity.

Preferred imidazoliniums are those which have not more than twelve, preferably not more than ten carbon atoms.

As far as the substrates are concerned, the substrate for exchange on aliphatic carbons is advantageously a substrate comprising an $sp^3$ hybridized halogen-bearing carbon which carries at least two halogens, of which at least one is a halogen with an atomic number greater than that of fluorine, it being possible for the two other substituents on the carbon to be two alkyls, one chalcogen atom or one other halogen atom which carries a doublet, or else one aryl and one alkyl, or else two aryls. However, it has been found that the reaction proceeded better when, firstly, said halogen-bearing carbon carried no hydrogen, secondly, when it carried either a chalcogen capable of supplying a doublet under proper conditions, in other words a chalcogen in an oxidation state of minus two, generally an ether or an ester, or equivalents thereof in which the oxygen is replaced by a sulfur.

Another series of compounds giving good results is the case in which the halogen-bearing carbon is connected to at least one low-hybridization atom which carries an unsaturation. Apart from the case in which said low-hybridization atom which carries an unsaturation is engaged in a carbon-carbon bond (acetylenic bond, preferably ethylenic bond, this ethylenic bond advantageously forming part of an aromatic ring), it is possible to indicate, by way of teaching by example, that, advantageously, said low-hybridization atom which carries an unsaturation is an atom involved in one of the following double bonds [where *C is the halogen-bearing carbon]:

| Low-hybridization atom and unsaturation which it carries | Degree of ease of the exchange reaction(easy = 1; less easy = 2 but more selective; relatively difficult = 3) |
|---|---|
| —*C—CR"=NR' | 2 |
| —*C—CR"=S' | 1 |
| —*C—C=N—NH—R' | 2 |
| —*C—CR"=N—O—R' | 2 |
| —*C—CR"=PR' | 2 |
| —*C—N=NR' | 2 compounds which are sometimes fragile, thereby limiting the range of acceptable operating conditions |
| —*C—CF=CF$_2$ | 2 risk of polymerization |
| —*C—CR="O | 3 reaction difficult |
| —*C—N=O | 2 may give rise to very complex mixtures |

Accordingly, the general formula of the substrate may be written as follows:

R—CX'X'"-X" where R is selected from hydrocarbon residues (i.e., residues containing carbon and hydrogen, especially aryl or alkyl), halogens, electron-withdrawing (preferably by inductive effect) groups;

with X' selected from halogens, preferably chlorine;

with X'" selected from halogens, preferably chlorine; with the condition, of course, that R, X and X' cannot simultaneously be fluorine, and that one of them represents at least one heavier-than-fluorine halogen to be exchanged with the fluorine, preferably chlorine;

with X" selected from aryls, halogens, alkyloxy, thioalkyloxy, acylalkyloxy, thioacylalkyloxy, aryls and alkyls and by a radical of the following formula:

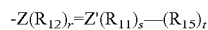

to form the substrate of formula

       (I)

Z is selected from trivalent semimetals, with r being zero, or tetravalent semimetals, with r being 1 (respectively phosphorus, advantageously nitrogen on the one hand and carbon on the other hand, preferably carbon);

and Z' is selected from semimetals, advantageously chalcogens (with s and t being zero), nitrogen and phosphorus (with s being zero) and carbon, with s and t being 1);

r, s, and t may adopt the values zero or one, depending on the meaning of Z and Z'.

Surprisingly, R can be hydrogen and can give rise to easy exchange, especially when the compound is of formula two, preferably when Ar is homocyclic.

R may also be of type -Z($R_{10}$)$_r$=Z'($R_{11}$)$_s$—($R_5$)$_t$, including of type Ar ($R_{11}$)$_s$, to give a symmetrical molecule or not. $R_{15}$ may be hydrogen or any radical, advantageously a hydrocarbon radical (i.e., a radical containing carbon and hydrogen).

$R_{12}$ may independently take the same values as $R_{15}$ $R_{11}$ may independently take the same values as $R_{15}$ however, in accordance with the present invention, $R_{12}$ and $R_{15}$ are advantageously connected to form an aromatic ring, thereby producing the case in which X" is aromatic.

According to the present invention it is preferable for R, X' and X'" to be such that between them they have at least two halogens other than fluorine and that they have at least one halogen which is chlorine.

It is also preferable for R and X" to be such that one of the two is aromatic, halogen, advantageously other than fluorine, a radical connected by a chalcogen to the halogen-bearing carbon (i.e., the carbon carrying X'" and X') or a radical which carries a double bond, such that the halogen-bearing carbon is in position.

As has been shown above, the halogen-fluorine exchange reactions, preferably and most frequently chlorine-fluorine exchange reactions, are particularly selective when in the general formula n is one. In order to obtain selectivity it is sufficient alternatively to limit the amount of the nucleophile, generally the fluoride, or to limit the temperature, or to limit the duration. As will be seen in the examples, this selectivity of the exchanges is particularly impressive. The nucleophiles are those which have already been mentioned in the body of the present description, particularly the anionic, or even neutral, nucleophiles for which the pKa for the associated acid is not more than 4 when the nucleophile is a fluoride, the fluorides can be introduced in the form of an alkali metal fluoride, preferably an alkali metal fluoride in which the alkali metal is superior or equal to that of sodium, preferably at least equal to that of potassium. The fluoride ions may also be introduced in the form of the co-anion of the compound of formula G or, finally, can be introduced in the form of ammonium or phosphonium.

As has been seen above, the co-anions are preferably co-anions corresponding to very strong acids, especially those whose Hammett constant is greater than or equal to that of trifluoroacetic acid.

However, as has already been mentioned, it is possible to use, on the one hand, as co-anion, the anionic nucleophiles which are to act on the substrate.

However, as has already been mentioned, it has been shown that the co-anions most common for ionic liquids, namely complex anions such as $BF_4^-$ and $PF_6^-$, give results, which although good, are not the best. The same is true of the anions of the perfluoroalkane sulfonic type and the corresponding imides such as triflimide.

As acid of the perfluoroalkane sulfonic type it is appropriate to mention sulfonic acids which carry a difluorinated carbon, the remainder of the molecule being arbitrary provided it does not react.

The preferred anions are the anions corresponding to the heavy halides (iodide, chloride and bromide) and more particularly to the chlorides and to the bromides. For exchange by $SN_2$ on an $sp^3$ carbon which carries at least two halogens of which at least one is chlorine, the bromide is preferred.

In the case of chlorine-fluorine exchange on an aliphatic carbon (i.e., a carbon with $sp^3$ hybridization) the bromides are those which have given the best results, with the exclusion of the fluorides which play the part both of nucleophiles and of co-anions.

In any case, the presence of the bromide ion in exchanges on aliphatic carbons is eminently beneficial. Its role starts to be manifested and becomes significant when its molar ratio between the bromide and the cation of formula G is at least 5%, preferably 10%.

The operating conditions are substantially the same as those which employ a conventional polar aprotic solvent, such as sulfolane. It is, however, possible to lower the temperature slightly, owing to the high reactivity of the reaction medium according to the present invention.

It is advantageous to note that it is preferable, among the compounds of the class of formula G1, to use those which are immiscible with water in any proportion, which facilitates the purification of these compounds of formula G1 which, it will be recalled, are in principle undistillable.

In the case of $SN_2$ reactions for chlorine-fluorine exchanges on aliphatic substrates which carry a halogen-bearing carbon, the use of the compounds of formula G in which n is zero is, in so far as it has not been specified above, advantageously employed under the same conditions as the $SN_{Ar}$ substitutions on aromatic substrates, described below.

Another aim of the present invention is to provide a process for nucleophilic substitution, advantageously for aromatic nucleophilic substitution, which employs the present invention.

This aim, and others which will appear subsequently, is achieved by means of a process of nucleophilic substitution, characterized in that a substrate of general formula (III):

Ar—Ξ     (III)

where Ar is an aromatic radical in which the nucleus carrying Ξ is electron-poor, either because it contains at least one heteroatom in its ring (6-membered aromatic ring) or because the sum of the $\sigma_p$s of its substituents, apart from the Ξ in question, is at least 0.2, advantageously 0.4, preferably 0.5, and where Ξ is a leaving group, advantageously in the form of an anion Ξ$^-$, is contacted with a composition comprising, apart from the substrate, in a liquid phase, for successive or simultaneous addition:

(a) at least one compound of formula G, advantageously a quaternary phosphonium compound or a mixture of quaternary phosphonium compounds containing at least 4 carbon atoms (b) a co-anion, (c) a nucleophilic substituent, optionally in salt form, (d) further components, the molar ratio between the compound or compounds of formula G, advantageously (a) phosphonium compound(s) and the substrate ([P$^+$]/[sub]) being at least a 1/4, advantageously 1/3, preferably 1/2, more preferably 2/3. The sum of (a)+(b)+(c)+(d) represents 100% of said liquid phase.

It is preferable that any solvents, especially polar solvents, do not excessively dilute the at least one compound of formula G, advantageously one or more phosphonium compounds. Thus, when (d) comprises a solvent, this solvent is present in an amount such that the ratio by mass between the sum of the polar solvents and the sum of the salts of at least one compound of formula G, advantageously a phosphonium compound ([S.P.]/[P$^+$]), i.e., [S.P.]/(a+b), is not more than 1, advantageously than 1/2, preferably than 1/5. It is preferable for the restriction above to apply to all of the optional solvents, polar or non polar.

It ought to be explained that Ξ is not individualized except for the ease of writing the reaction and that Ar may carry at least one leaving group other than Ξ, it being possible for these leaving groups to be identical to or different from Ξ. Accordingly, in polychlorinated aromatics, one of the chlorines may play the part of leaving group while the others will play the part of electron-withdrawing groups; after exchange has been carried out, another chlorine could be the leaving group, and so on.

Thus in halogen exchange, particularly in polychorobenzenes or polychloropyridines, all of the chlorines may be successively substituted by fluorines, but the exchange will become more and more difficult as the chlorines are replaced by the fluorines, since the $\sigma_p$ (sigma p) of fluorine (0.15) is significantly less than that of chlorine (0.25).

The present invention is particularly appropriate for treating pyridine nuclei with a low level of impoverishment, such that the sum of the $\sigma_p$ (Hammett constant) of the substituents of Ar, excluding Ξ is not more than 1, advantageously than 0.8, preferably than 0.6.

One of the cases in which the invention allows better treatment than the others is that in which Ar is such that the aromatic nucleus carrying Ξ is a 6-membered nucleus whose electron-withdrawing groups are groups which withdraw electrons by inductive and not mesomeric effect.

Thus the process of the present invention is highly suitable in the case in which Ar is such that the aromatic nucleus carrying Ξ is a 6-membered nucleus whose electron-withdrawing groups are for the most part, or even solely, halogens, advantageously chlorine and fluorine.

The process according to the present invention allows treatment in cases in which Ar is such that the aromatic-nucleus carrying Ξ is a 6-membered nucleus in which the electron-withdrawing group or at least one of the electron-withdrawing groups is positioned meta relative to Ξ and is advantageously a chlorine and/or a fluorine.

Advantageously Ξ is less nucleophilic than the nucleophilic agent with which it will be exchanged; since nucleophilicity scales are difficult to use, it will be possible for the skilled worker to use the empirical rule that ΞH is advantageously more acidic than the nucleophile in protonated form. Ξ may be a nitro or quaternary ammonium group; however, it is preferable for it to be either a pseudohalogen group or, preferably, a halogen atom selected from chlorine, bromine, and iodine.

By pseudohalogen is meant a group whose departure leads to an oxygenated anion, the anionic charge being carried by the chalcogen atom, whose acidity, expressed in terms of the Hammett constant, is at least equal to that of acetic acid, advantageously to the second acidity of sulfuric acid, and, preferably to that of trifluoroacetic acid.

To illustrate this type of pseudohalogens, mention may be made in particular of the anions corresponding to sulfinic and sulfonic acids which are advantageously perhalogenated on the sulfur-bearing carbon, and also carboxylic acids perfluorinated α to the carboxyl function.

Since the nucleophilic substitution reaction is facilitated relatively when Ξ represents an iodine atom, the process claimed is of more particular advantage when Ξ symbolizes a chlorine or bromine atom or a pseudohalogen.

As far as the substituent or substituents Ar, sometimes denoted "groups R", are concerned, it (they) is (are) present on the aromatic nucleus; it (they) is (are) selected such that, overall, it (they) induces (induce) electron impoverishment in the nucleus, which is sufficient to allow the substrate to be activated and the Meisenheimer complex to be stabilized (cf. indication given above).

The aromatic substrate thus substituted possesses an electron density which is at most equal to that of phenyl, advantageously closer to that of a chlorophenyl and, preferably, a difluorophenyl.

This impoverishment may also be due to the presence in the aromatic ring of a heteroatom, such as, for example, in pyridine, quinoline. It is important to stress that this type of impoverishment is observed only when. Ar symbolizes a compound having a 6-membered ring and the heteroatom belongs to group V (essentially nitrogen or phosphorus) as defined in the table of the periodic classification of the elements published in the supplement to Bulletin de la Société Chimique de France in January 1966.

Most frequently the group R, or at least one of the groups R, is an electron-withdrawing, non-leaving substituent and more preferably is not a carbonic constituent.

The substituent or substituents R, when it (they) has (have) a withdrawing effect, can be selected from halogen atoms and the following groups:

$NO_2$
$SO_2Alk$ and $SO_3Alk$
Rf and preferably $CF_3$
CN
CHO
COAlk
COΞ', where Ξ' is selected from the same values as Ξ, with the same preferences
COOAlk
phosphonyl and phosphonate, the symbol Alk representing a hydrogen, advantageously a linear or branched, preferably $C_1$ to $C_4$, alkyl group.

As examples of preferred groups R mention may be made more particularly of halogen atoms and the nitro group.

The electron-withdrawing substituent or substituents R are more preferably positioned ortho and/or para to the leaving group(s) Ξ.

As regards the nucleophilic agent which is intended to replace the leaving group(s) X on the aromatic substrate, it may be generated in situ during the irradiation reaction.

As a nucleophilic agent which can be used in accordance with the invention mention may be made in particular of the following:
   phosphine, arsine, ammonia,
   phosphines, arsines, amines and their anions,
   water and its anion,
   alcohols and alkoxides,
   hydrazines, semi-carbazides,
   salts of weak acids, such as carboxylates, thiolates, thiols, carbonates,
   cyanide and its salts,
   malonic derivatives, and
   imines.

The nitrogen nucleophile derivatives are of very particular interest in the context of the claimed process.

The nucleophilic agents whose nucleophilic function is an anion give good results.

Another aim of the present invention is to provide a process useful particularly for carrying out exchange reactions between fluorine and halogens having a higher atomic number which are present on the aromatic substrate, and especially exchange reactions between fluorine and chlorine.

Inverse exchange reactions, in other words the replacement of one halogen by a higher-ranked halogen, are likewise possible. This type of reaction, however, carries less interest and, moreover, is more difficult to carry out. Nevertheless, it is within the ability of the skilled worker to exploit the teaching of the present process to carry out other exchange reactions, and in particular these inverse exchange reactions.

In the case of exchange reactions between fluorine and halogens of higher atomic number, preference will be given to using a fluoride as nucleophilic agent.

The fluoride is advantageously a fluoride of an alkali metal with an atomic number at least equal to that of sodium, and is preferably a potassium fluoride.

The alkali metal or alkaline earth metal fluoride is at least partly present in the form of a solid phase.

Generally speaking, the reaction is conducted at a temperature lower than that for a reaction conducted under the customary conditions.

Although not preferred, the reaction can be conducted in the presence of a solvent.

It is also possible to recover the more volatile compounds continuously as they are formed. This recovery may be carried out, for example, by distillation.

According to one of the possible embodiments, heating is carried out partly or totally by microwaves of the present invention; in this case it is preferable for the microwaves to be emitted in short periods (from 10 seconds to 15 minutes) alternating with cooling phases. The respective durations of the microwave emission periods and of the cooling periods are selected such that the temperature at the end of each microwave emission period remains lower than a fixed initial temperature, which is generally less than that of the resistance of the ingredients of the reaction mixture.

It is likewise possible to carry out such heating in accordance with a procedure in which the reaction mixture is subjected simultaneously to microwaves and to cooling. In accordance with this version the power emitted by the microwaves is selected such that, for a fixed initial temperature, generally the operating temperature, said power is equivalent to the energy removed by the cooling system, which is in turn approximately equivalent to the heat given off or absorbed by the reaction.

An actinic heating process of this kind, moreover, has the advantage of being compatible with a continuous operating mode. This mode of use makes it possible, advantageously, to avoid the heat exchange problems which can occur during operations of opening and closing the reactor in which the microwaves are emitted.

In accordance with this operating mode, the materials to be activated are introduced continuously via an inlet orifice within the reactor, where they undergo activation by microwaves, and the activated products are evacuated continuously from said reactor via an outlet orifice.

In the case of actinic heating by microwaves it is recommended to use a power emitted by the microwaves of between 1 and 50 watts per milli equivalent of aromatic substrate. It is likewise desirable to conform to the constriction whereby the power emitted by the microwaves is between 2 and 100 watts per gram of reaction mixture.

The medium according to the invention may be used concomitantly with a catalyst known to be a phase transfer catalyst, especially when said catalyst is a cationic catalyst. It may in particular comprise cations which are bound, for example, by crown ethers which bind alkali metals.

These phase transfer catalysts may be used in the presence or absence, preferably in the presence, of a particularly heavy alkali metal cation which therefore has a high atomic ranking, such as cesium and rubidium.

The amount of alkali metal cation, when it is used as a promoter, is advantageously between 1 and 5%, preferably between 2 and 3%, in terms of the number of moles of nucleophilic agent employed. These ranges are closed ranges: that is, they include their boundaries.

The reagent may comprise as promoter phase transfer agents which are onium compounds (organic cations whose name ends in onium). The onium compounds represent generally 1 to 10%, preferably from 2 to 5% in terms of the number of moles of the aromatic substrate; the counterion is arbitrary but most often contains halogen.

In the present description onium compounds are defined as being compounds selected from the group of cations formed by groups VB and VIB as defined in the table of the periodic classification of the elements published in the supplement to Bulletin de la SociétéChimique de France in January 1966, having respectively four (group VB) and (group VIB) or three hydrocarbon chains. These phase transfer agents are customarily used when the reaction mixture includes at least two condensed phases (recalling that "condensed phase" covers liquid and solid phases) in the present invention these agents are of much less interest, since a large number of phosphonium compounds are considered as being phase transfer agents.

Preferred among the onium compounds are tetraalkylammoniums of 4 to 28 carbon atoms, preferably of 4 to 16 carbon atoms. The tetraalkylammonium is generally tetramethylammonium. It should, however, be noted that the advantage of such compounds in the medium according to the present invention is of much less interest than in the customary art.

According to the invention the polar aprotic solvents are those which advantageously have a significant dipole moment and a relatively high donor number. Thus, its relative dielectric constant epsilon is advantageously at least equal to approximately 10, epsilon being preferably less than or equal to 100 and greater than or equal to 25, and its donor index is between 10 and 50, said donor index being the $\Delta H$ (enthalpy change), expressed in kilocalories, of the combination of said dipolar aprotic solvent with antimony pentachloride. According to the present invention these solvents play a part as further solvent, but their presence is detrimental to the kinetics of the reaction, and their proportion must be limited to the values specified above.

Generally it is known that a fine granulometry has an influence on the kinetics. Accordingly it is desirable for said solid in suspension to have a granulometry such that its $d_{90}$ (defined as the mesh size which allows 90% by mass of the solid to pass) is not more than 100 μm, advantageously not more than 50 μm, preferably not more than 200 μm. The lower limit is advantageously characterized in that the $d_{10}$ of said solid in suspension is at least 0.1 μm, preferably at least 1 μm.

The ratio between said nucleophilic agent, preferably the alkali metal fluoride, and said substrate is generally between 1 and 1.5, preferably around 5/4 relative to the stoichiometry of the exchange.

The mass fraction of solids present in the reaction medium is advantageously at least 1/5, advantageously 1/4, preferably 1/3.

Stirring is advantageously carried out such that at least 80%, preferably at least 90%, of the solids are maintained in suspension by stirring.

According to the present invention the reaction is advantageously conducted at a temperature ranging from approximately 150 to approximately 250° C. In the present description the term "approximately" is employed to emphasize the fact that the values which follow it correspond to values which have been rounded off mathematically and, in particular, that in the absence of a decimal point, when the figure or figures furthest to the right of a number are zeros, these zeros are positional zeros and not significant figures, unless, of course, it is otherwise specified.

It should be underlined, however, that when the temperature increases the kinetics increase but the selectivity decreases.

The examples which follow illustrate the invention.

I. $SN_{Ar}$ Exchange

A 5 ml round-bottomed flask surmounted by a wheel-type condenser is charged with 3 equivalents of KF and 0.4 equivalent of tetramethylammonium chloride in an ionic solvent, namely methylbutylimidazolinium, i.e., or $R_1$ is methyl and/or $R_6$ is butyl. The coanion is $PF_6-$. The contents of the flask are dried at 100° C. under vane pump vacuum ($10^{-2}$ mm of mercury) and with magnetic stirring for 3 h. One equivalent of the substrate is added and the mixture is heated at 150° C. for 24 h. It is subsequently cooled to ambient temperature and then the reaction mixture is extracted three times with 3 ml of ethyl ether. This solution is assayed by gas chromatography and then a check is carried out by NMR using the isotope 19 of fluorine in order to identify the products of the reaction.

EXAMPLE 1 para-Chloronitrobenzene Substrate

The manipulation was carried out on the one hand on commercial potassium fluoride and on the other hand on ultradry KF obtained by atomizing aqueous potassium fluoride solution at more than 3000. In the case of the commercial fluoride, this gives 60% of the fluorinated product and 40% of the starting product in the same uses of atomized potassium fluoride improve the results slightly.

EXAMPLE 2

Action on Trichloronitrobenzene

The general procedure is repeated, changing the amounts of KF and tetramethylammonium chloride: here, 2 equivalents of KF and 1 equivalent of tetramethylammonium chloride are used and 18% of the starting product, 35% of the mono-ortho-substituted product, 6% of the mono-para-substituted product, and 31% of the difluorinated product are recovered. Comparisons involving lowering the proportion of phase transfer agent show that it is of relatively little importance.

EXAMPLE 3

Comparison Between Different Ionic Solvents

The comparison is conducted between:
  butylmethylimidazolinium, referred to hereinafter as Bmim with $PF_6^-$ as coanion;
  linear $C_8$ N-octylmethylimidazolinium; this cation will be referred to below as $C_8$mim, with $BF_4^-$ as coanion;
  butyldimethylimidazolinium, referred to hereinafter as Bdim, with $BF_4^-$ as coanion;
  ethylmethylimidazolinium, referred to hereinafter as Emim, in bromide form;
  and sulfolane, which represents the prior art.

It should be noted that, when there are two substituents on the imidazole, these two substituents are situated on each of the nitrogens. When there is a third substituent, it is substituted on the carbon situated between the two nitrogens, and corresponds, in the nomenclature of the present description, to $R_5$.

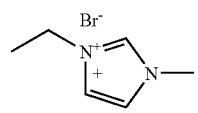

EmimBr m.p. 79-81° C.; soluble in water, soluble in $CH_2Cl_2$, insoluble in $Et_2O$.

Comparison with $BmimPF_6$, $C8mimBF_4$, $BdmimPF_6$, and Sulfolane

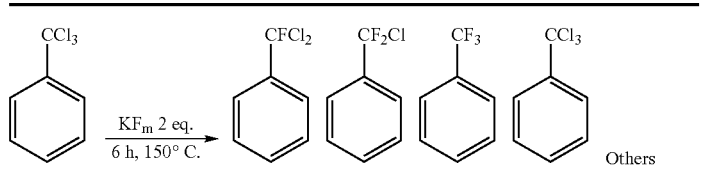

| | $CCl_3$ | $CFCl_2$ | $CF_2Cl$ | $CF_3$ | $CCl_3$ Others |
|---|---|---|---|---|---|
| $BmimPF_6$ | 94% | 5% | 0% | 0% | 1% |
| $BdmimPF_6$ | 38% | 7% | 0% | 35% | 20% |
| $C_8mimBF_4$ | 82% | 3% | 0% | 2% | 13% |
| EmimBr | 21% | 63% | 5% | 0% | 11% |
| Sulfolane | 8% | 5% | 0% | 86% | 1% |

(by GC)

The much higher reactivity in the EmimBr solvent is even better illustrated by the following comparison:

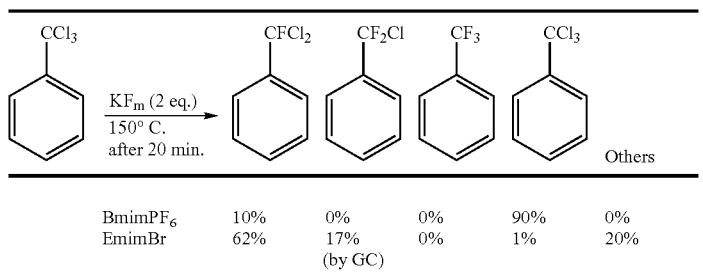

|  | CFCl$_2$ | CF$_2$Cl | CF$_3$ | CCl$_3$ | Others |
|---|---|---|---|---|---|
| BmimPF$_6$ | 10% | 0% | 0% | 90% | 0% |
| EmimBr | 62% | 17% (by GC) | 0% | 1% | 20% |

EXAMPLE 4

Selectivity Toward the Monofluorinated Compound

The aim here was to find out whether the more effective solvent from the kinetic standpoint allowed a good selectivity for obtaining a monofluorinated compound, in particular using a reduced amount of potassium fluoride.

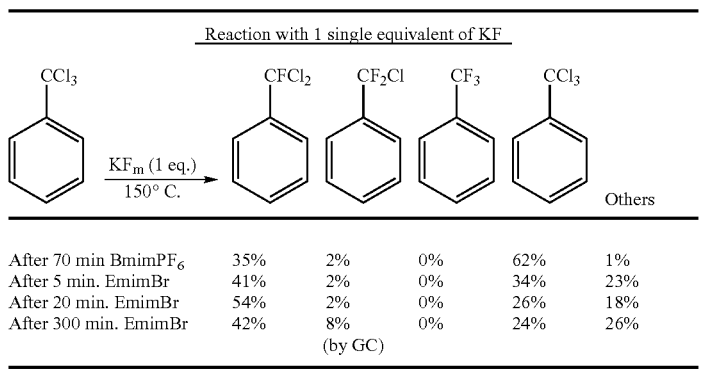

Reaction with 1 single equivalent of KF

|  | CFCl$_2$ | CF$_2$Cl | CF$_3$ | CCl$_3$ | Others |
|---|---|---|---|---|---|
| After 70 min BmimPF$_6$ | 35% | 2% | 0% | 62% | 1% |
| After 5 min. EmimBr | 41% | 2% | 0% | 34% | 23% |
| After 20 min. EmimBr | 54% | 2% | 0% | 26% | 18% |
| After 300 min. EmimBr | 42% | 8% (by GC) | 0% | 24% | 26% |

As in the BmimPF$_6$ solvent, with 1 equivalent of KF the reaction blocks.

For EmimBr the maximum is reached after 20 minutes; after 6 h of reaction it is observed that the consumption of trichlorotoluene has hardly changed. In relation to the BmimPF$_6$ solvent it is observed that the consumption of the starting product is markedly higher.

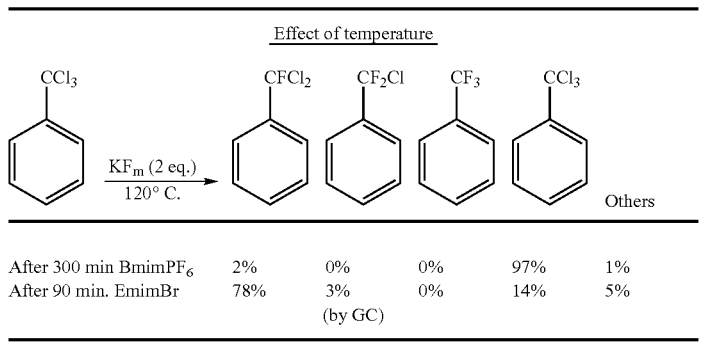

Effect of temperature

|  | CFCl$_2$ | CF$_2$Cl | CF$_3$ | CCl$_3$ | Others |
|---|---|---|---|---|---|
| After 300 min BmimPF$_6$ | 2% | 0% | 0% | 97% | 1% |
| After 90 min. EmimBr | 78% | 3% (by GC) | 0% | 14% | 5% |

EXAMPLE 5

Synthesis of the Difluorinated Compound

| | CFCl$_2$ | CF$_2$Cl | CF$_3$ | CCl$_3$ | Others |
|---|---|---|---|---|---|
| After 10 min EmimBr | 30% | 57% | 4% | 1% | 8% |
| After 200 min. EmimBr | 4% | 77% (by GC) | 12% | 0% | 7% |

Starting material: CCl$_3$-phenyl, KF$_m$ (3 eq.), 150° C.

In the light of these results it is realized that it is possible to obtain the monofluorinated and difluorinated compounds selectively. Access to the trifluorinated compound is also possible.

It is realized that for the fluorination reaction under study it is possible to determine 3 types of solvent at this stage:

highly reactive solvent: EmimBr
reactive solvent: EmimPF$_6$>BmimPF$_6$, BmimBF$_4$>C$_8$mimPF$_6$, C$_8$mimBF$_4$
slightly less reactive solvent: BmimCl, BmimTf$_2$N The anion and the length of the alkyl chain influence the result.

By lengthening the alkyl chain (increasing the hydrophobic character), the reactivity is reduced.

EXAMPLE 6

Properties of Different Imidazolinium Compounds Tested

EXAMPLE 7

Study of Different Ionic Solvents in the Monofluorination of Phenylchloroform Preparation of ionic solvents

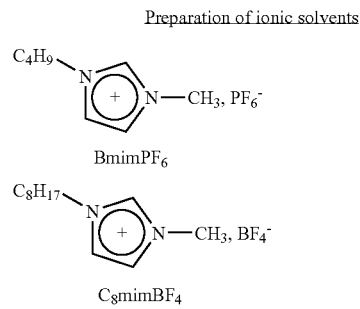

BmimPF$_6$

C$_8$mimBF$_4$

| | | Viscosity (cP) | Density (kg/l) | Solubility | | | | | Stability | |
|---|---|---|---|---|---|---|---|---|---|---|
| | | | | water | CH$_2$Cl$_2$ | EtOAc | Et$_2$O | Toluene | m.p. | Air | Thermal |
| C$_n$MIMBF$_4$ | n = 2 | 37.7 (295 K) | 1.24 (295 K) | s | s | | | | 12° C. | hygroscopic | 300° C. |
| | n = 4 | 233 (303 K) | 1.17 (293 K) | s | s | | | | (−)78° C. | hygroscopic | 300° C. |
| | n = 6 | | | | ins | s | | | (−)82° C. | hygroscopic | |
| | n = 8 | | | | ins | s | | | (−)79° C. | hygroscopic | |
| C$_n$MIMPF$_6$ | n = 2 | | | | ins | | | | 62° C. | hygroscopic | |
| | n = 4 | 312 (303 K) | 1.37 (303 K) | ins | s | s | ins | ins | (−)61° C. | hygroscopic | |
| | n = 6 | | | | ins | | | | | | |
| | n = 8 | | | | ins | | | | | | |
| C$_n$MIMCl | n = 2 | | | | s | | | | 87° C. | | |
| | n = 4 | | | | s | | ins | | 65-69° C. | | |
| | n = 6 | | | | s | | | | | | |
| C$_n$MIMCF$_3$SO$_3$ | n = 2 | 4.9 (298 K) | 1.39 (298 K) | s | s | s | | ins | (−)9° C. | | |
| | n = 4 | 90 (293 K) | 1.29 (293 K) | s | s | s | | ins | 16° C. | | |
| C$_n$MIM(CF$_3$SO$_2$)N | n = 2 | 34 (293 K) | 1.52 (295 K) | ins | s | s | | ins | (−)3° C. | | >400° C. |
| | n = 4 | 52 (293 K) | 1.429 (292 K) | ins | s | s | | ins | (−)4° C. | | | s = soluble
ins = insoluble

-continued

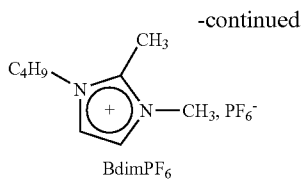

BdimPF$_6$

EXAMPLE 7a

Preparation of Ionic Solvents

Various procedures have been described in the literature for the synthesis of ionic solvents. As regards ionic solvents possessing an imidazole cation, the synthesis starts with the formation of the halide, with condensation of the imidazole and the corresponding haloalkane (Scheme 2).

Scheme 2

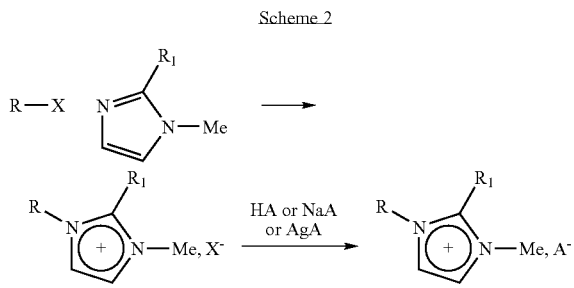

The second part of the synthesis involves exchanging the chloride ion for the desired anion; 3 methods have been described in the literature:

by reaction with the corresponding acid (e.g.: HPF$_6$);
  Problem: presence of acid in the final ionic solvent.
by reaction with the corresponding sodium salt (e.g.: NaBF$_4$);
  Problem: the reaction is often incomplete and C$_n$mimCl is miscible in C$_n$mimA.
by reaction with the corresponding silver salt (e.g.: AgBF$_4$);
  Problem: this method is limited owing to the price of the silver salts used (e.g.: AgBF$_4$ 5 g/514 Francs Aldrich).

The method utilizing the acidic solution has the advantage of being a complete reaction and the traces of acids can be removed if care is taken to wash the ionic solvent formed with water until the pH is neutral. If the solvent is stored for a long period it is useful to wash it again with water prior to use.

It has been shown that filtration on silica gel and washing with sodium carbonate allows a better purity to be achieved, especially in the case or the anion exchange reaction has been carried out using the sodium salt.

For our study we synthesized our solvents using anionic exchange by means of an acidic solution of HPF$_6$ or HBF$_4$ as described below.

Procedure for bmimPF$_6$
(1-n-butyl-3-methylimidazolinium hezafluorophosphate)

1-Methyl-1H-imidazole (15 mol, 0.18 mmol) and 1-chlorobutane (19 ml, 0.18 mmol) were stirred at reflux at 70° C. for 72 h. The resulting liquid was allowed to cool to ambient temperature and then washed with ethyl acetate (3×50 ml). The residual traces of ethyl acetate were removed by suction under vacuum followed by dilution of the viscous liquid in water (100 ml). Hexafluorophosphoric acid (30 ml of a 60% solution in water, 0.2 mol) was added cautiously to the resulting emulsion in order to avoid a violent release of temperature, and then the mixture was stirred overnight. The two phases were separated and the ionic liquid was washed with aliquots of water (30 ml) until this washing water was no longer acidic. The mixture was then heated under vacuum at 70° C. in order to remove the traces of water and to give the ionic liquid BmimPF$_6$ (47 g, 92% yield). Finally, the ionic liquid BmimPF$_6$ in solution in dichloromethane (50 ml) was passed over silica gel, after which the silica gel was washed a number of times with dichloromethane (5×20 ml), giving colorless BmimPF$_6$ (39 g, 76% yield).

The other ionic solvents C$_8$mimBF$_4$ and BdimPF$_6$, were prepared by following this method using the corresponding starting products. All of them were analyzed by fluorine NMR, proton NMR, carbon NMR and phosphorus NMR (for the PF$_6$ anions).

EXAMPLE 7b

Reactivity of the Various Ionic Solvents

Scheme 3
In BmimPF$_6$

CCl$_3$-C$_6$H$_5$ →(KF$_{rh.}$ (2 eq.), bmimPF6, 6 h, 150° C.)→ CFCl$_2$-C$_6$H$_5$ + CF$_2$Cl-C$_6$H$_5$ + CCl$_3$-C$_6$H$_5$ + Others

| | CFCl$_2$ | CF$_2$Cl | CCl$_3$ | Others |
|---|---|---|---|---|
| 1 mmol | 94% | 5% | 0% | 1% (by GC) |
| 10 mmol | 94% | 5% | 0% | 1% (by GC) |

The monofluorination reaction is complete, using 2 equivalents of potassium fluoride, after 6 h at 150° C. At the start of reaction the ionic solvent takes on a red coloration, which persists even after washing with water and ether, but proton NMR indicates that the solvent is clean.

Effect of the Catalyst

Tetramethylammonium chloride was used in the preliminary studies to catalyze this reaction. However, under the conditions described here, for the monofluorination reaction, the catalyst has no effect on the kinetics of the reaction, as can be seen by comparing the following plots (graph 1):

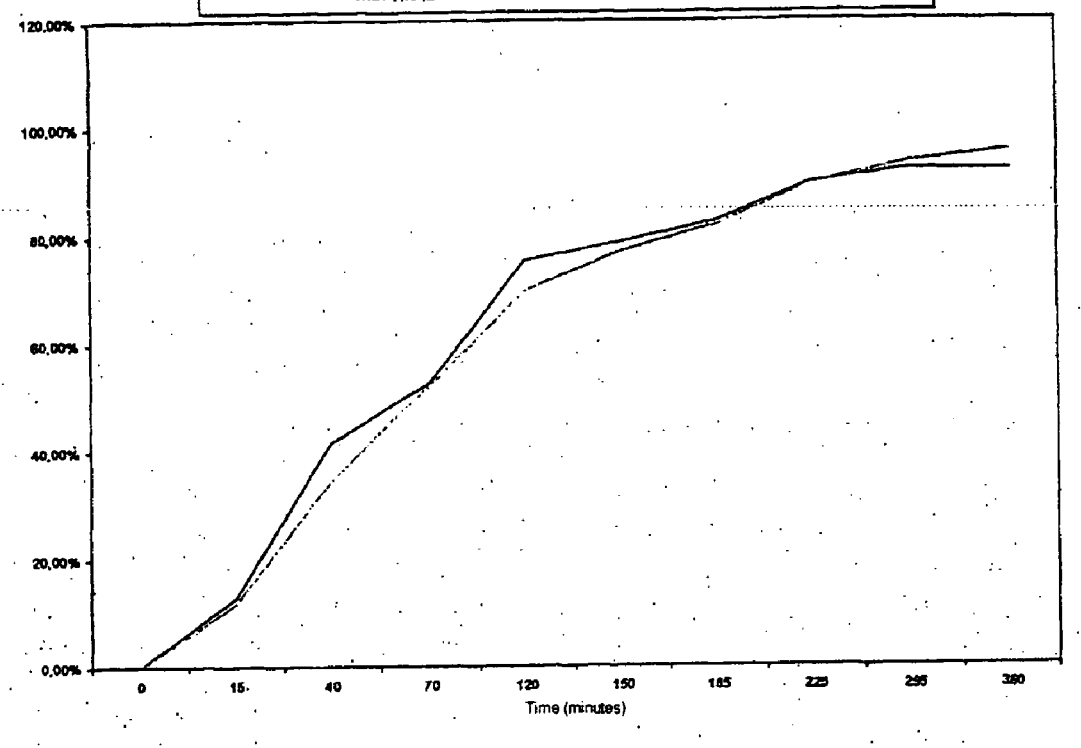
Graph 1

Amount of KF

With 1.5, equivalents of $KF_{rh}$ the reaction slows: 70% of $PhCFCl_2$ and 30% of $PhCCl_3$ (Graph 2).

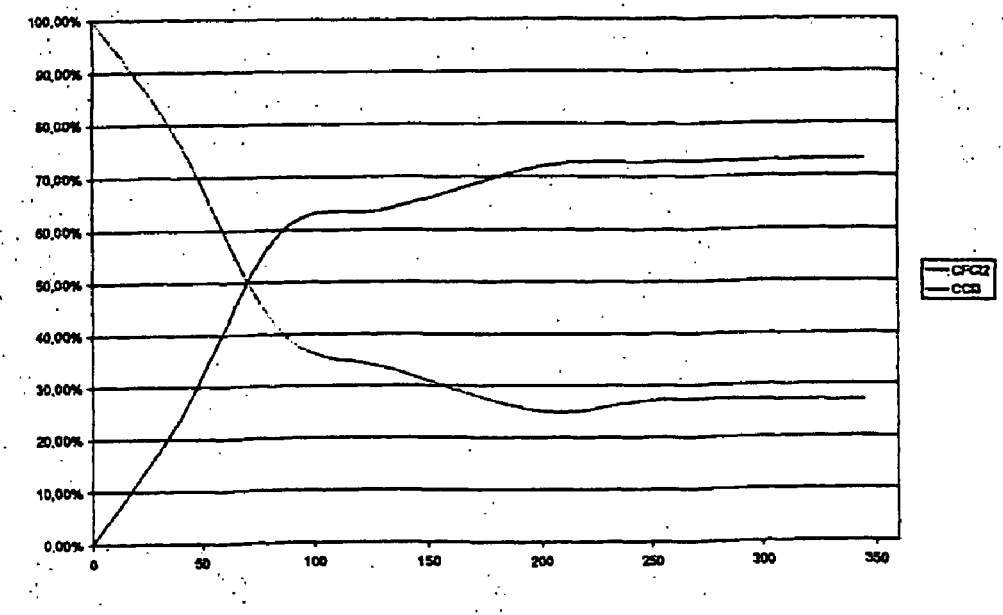
Graph 2

Under the same conditions, with 1 equivalent of $KF_{rh}$ the reaction slows: 34% of $PhCFCl_2$ and 66% of $PhCCl_3$ (Graph 3).

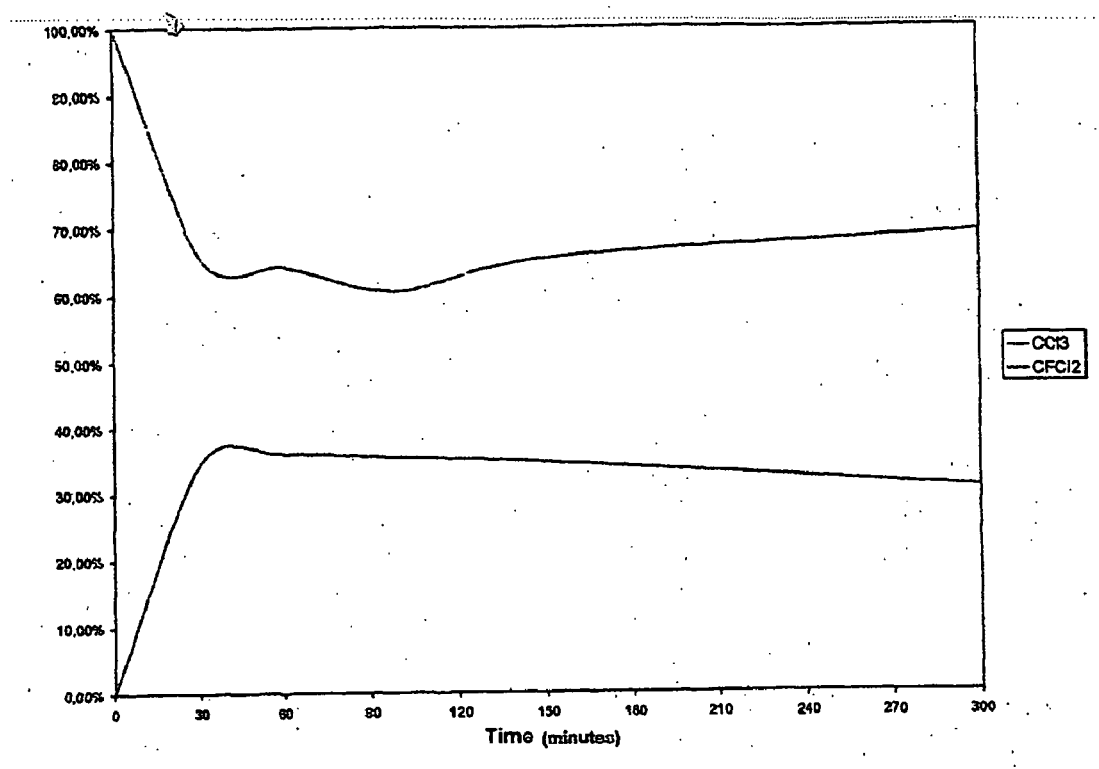
Graph 3

EXAMPLE 8

Recycling of the BmimPF$_6$ Solvent

The procedure used for each reaction is as follows:

A suspension of 116 mg (2 mmol) of potassium fluoride in 2 ml of butylimidazolinium hexafluorophosphate was stirred at 100° C. for 1 h under a vacuum of 0.1 mm of mercury.

After the vacuum has been replaced by nitrogen the mixture is taken to 150° C. and then 142 µl of phenylchloroform (1 mmol) are introduced were added, and the reaction mixture was heated at 150° C. for 6 h. The organic substances were extracted three times with 3 ml of diethyl ether. The ionic liquid was washed three times with 3 ml of cold water. The ionic liquid was then heated again at 100° C. for 1 h under vacuum before being reused as before.

EXAMPLE 9

Comparative Tests on the Effect of the Amount of Melting Salts on the Progress of the Reaction Procedure:

The following are introduced into a 60 ml tube:

1,3,5-trichlorobenzene: 0.5 g (2.8 mmol)

sulfolane 0.2 g

KF (atomized): 0.51 g (3.1 molar equivalents/TCB)

Bu4PBr: variable amount depending on test: see table.

The tubes are closed with a septum and a screw stopper then heated with stirring at 230° C. for 3 hours. On returning to ambient temperature the organic compounds are dissolved in dichloromethane and analyzed by GC.

| Tests | Molar eq of Bu4PBr/TCB | Yield % | Yield % DFCB | Yield % TFB | % Cl/F exchange accomplished (DCFB, DFCB, TFB) | Ratio between % of Cl/F exchange accomplished and molar amount of Bu4PBr/TCB |
|---|---|---|---|---|---|---|
| 1 | 0.26 | 4 | 0 | 0 | 1 | 0.15384615 |
| 2 | 0.51 | 20 | 0 | 0 | 7 | 0.39215686 |
| 3 | 0.77 | 60 | 21 | 0 | 34 | 1.32467532 |
| 4 | 1.03 | 38 | 35 | 2 | 38 | 1.10679612 |
| 5* | 1.50 | 29 | 43 | 9 | 47 | 0.94666667 |
| 6* | 2.00 | 25 | 40 | 11 | 46 | 0.69 |

The values with a high degree of conversion to difluoro and especially to trifluoro are under evaluated, owing to the volatility of these compounds, leading on the one hand to a loss of the products formed and on the other hand to a lower residence time of the volatiles. These elements make the nonlinear effect of the Bu4PBr even more indisputable.

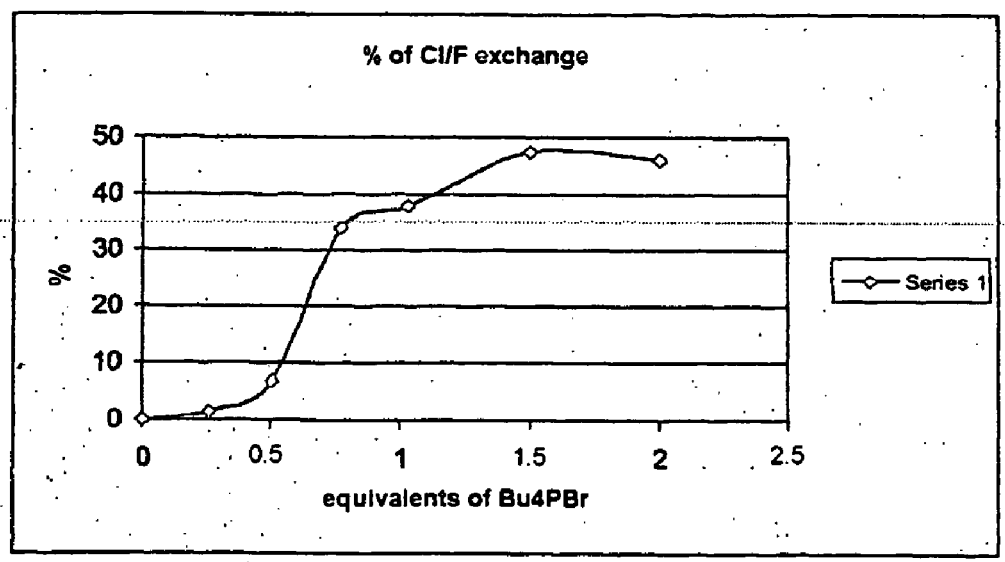

This nonlinear effect is also markedly apparent when the measurements are presented as follows:

TCB (1,3,5-trichlorobenzene) →KF→ FDCB (1-fluoro-3,5-dichlorobenzene) + DFCB (1-chloro-3,5-difluorobenzene) + TFB (1,3,5-trifluorobenzene)

| Molar ratio between phosphonium compound and substrate | 1st exchange (sum of the molecules having undergone at least one exchange) | 2nd exchange (sum of the molecules having undergone at least two exchanges) relative to the yield of the preceding exchange | 3rd exchange relative to the yield of the preceding exchange | Exchange achieved in total relative to the total exchangeable chlorine | Slope of the total exchange with the origin | Slope between two consecutive points | | |
|---|---|---|---|---|---|---|---|---|
| | | | | | | 1st exchange | 2nd exchange | 3rd exchange |
| 0 | 0 | 0 | 0 | | | | | |
| 0.26 | 4% | 0% | 0% | 1.00 | 0.15 | 0.15 | 0.00 | 0.00 |
| 0.51 | 20% | 0% | 0% | 7.00 | 600.39 | 0.64 | 0.00 | 0.00 |
| 0.77 | 81% | 26% | 0% | 34.00 | 1.32 | 2.35 | 1.00 | 0.00 |
| 1.03 | 75% | 49% | 3% | 38.00 | 1.11 | 0.23 | 0.90 | 0.10 |
| 1.50 | 81% | 64% | 11% | 47.00 | 0.95 | 0.13 | 0.32 | 0.18 |
| 2.00 | 76% | 67% | 14% | 46.00 | 0.69 | 0.10 | 0.06 | 0.07 |

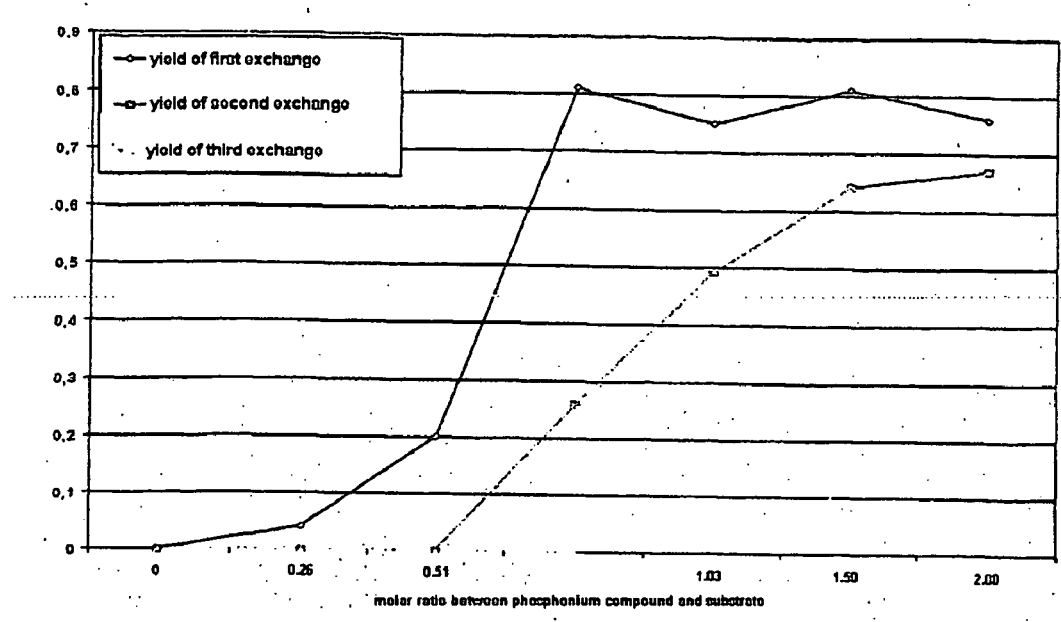

The S shape of the curves above shows that the effect of the phosphonium compounds is not linear and that the effect of the phosphonium compound at high ratios cannot be reduced to that of the low ratios. Starting from a ratio of the order of 1/4 and in particular of one third the increase in conversion becomes considerable.

EXAMPLE 10

Test in a Reactor With Ideal Stirring

A 500 ml reactor is charged with
TCB 61.5 g (0.34 mol)
KF 65.1 g (0.36 mol, 3.3 eq/TCB)
Bu4PBr 154.4 g (0.166 mol, 1.34 eq/TCB).

The mixture is heated to 120° C., placed under stirring (homogeneous suspension) and then heated at 190-210° C. for 4 hours. The volatile compounds formed during the reaction are distilled off continuously. The heating is then switched off and the reactor is placed under partial vacuum (150-200 mbar) so as to distill off the TCB and the FDCB.

Sum of the distillates recovered: m=48.4 g

| Aromatic organic balance, GC analysis: | | |
|---|---|---|
| Product | Total | molar % |
| TCB (mmol) | 19.5 | 5.7 |
| FDCB (mmol) | 132.4 | 39 |
| DFCB (mmol) | 118.4 | 35 |
| TFB (mmol) | 43 | 13 |
| Total | 313.3 | 92.7 |

EXAMPLE 11

Reaction of 1,3-dichlorobenzene

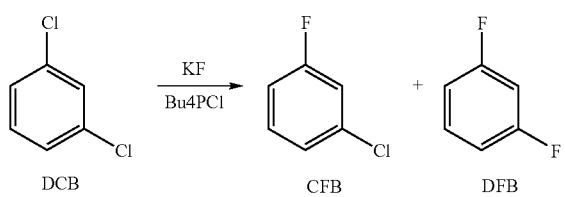

Procedure:

In a 200 mL reactor with ideal stirring, equipped with a thermometer and a distillation device, the following are introduced in this order:
KF: 12.50 g (2.11 equivalents/1,3-dichlorobenzene)
Bu$_4$PCl: 90.07 g (3.00 equivalents/1,3-dichlorobenzene)
1,3-dichlorobenzene: 14.99 g Reaction mixture is heated at 210-220° C. under a slight reflux for approximately 3 hours. Under atmospheric pressure a first fraction (1) is distilled off, and then a distillation is carried out under partial vacuum (to 33 mbar, 220° C. in the reaction mass), leading to fraction (2). Fractions 1 and 2 are combined and analyzed by HPLC.

Results:

Degree of Conversion of DCB=74.7%
Yield of CFB=55.3%
Yield of DFB=5.7%

EXAMPLE 12

Reaction of 1,2,4-trichlorobenzene

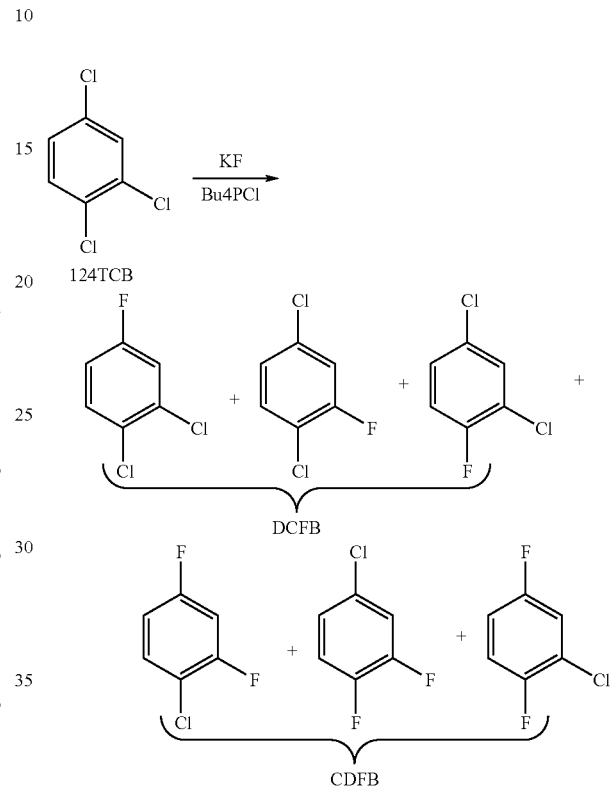

Procedure:

In a 200 mL reactor with ideal stirring, equipped with a thermometer and a distillation device, the following are introduced in this order:
KF: 13.8 g (1.5 equivalents/124TCB)
Bu$_4$PCl: 47 g (1 equivalent/124TCB)
1,2,4-trichlorobenzene: 29.8 g The reaction mixture is heated at 205-215° C. under a slight reflux for approximately 3 hours. Under atmospheric pressure a first fraction (1) is distilled off, and then a distillation is carried out under partial vacuum (to 280 mbar, 220° C. in the reaction mass), leading to fraction (2).

Fractions 1 and 2 are combined and analyzed by HPLC.

Results:

Degree of Conversion of 124TCB=80.4%
Yield of DCFB=45.2%
Yield of CDFB=5.5%

The invention claimed is:
1. A process for carrying out a nucleophilic substitution on an aromatic substrate, comprising the step of:
contacting said substrate of general formula (III):

$$Ar—\Xi \qquad (III)$$

wherein Ar is an aromatic group where the nucleus carrying the group $\Xi$ is electron-poor, either because it contains at least one heteroatom in its ring or because the sum of the Hammett constants, $\sigma_p$s, of its substituents, apart from said Ξ, is at least 0.2, and, wherein Ξ is a leaving group selected from the group consisting of halogens, pseudo halogens and a nitro group, optionally in the form of an anion Ξ;

with a composition used as a reaction medium for reacting said substrate, said composition comprising:

a) at least one ionic quaternary phosphonium compound whose cation is of general formula I':

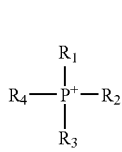

wherein $R_1$, $R_2$, $R_3$ and $R_4$, which are identical or different, are hydrocarbon radicals, and whose anion or anion mixture ensures electroneutrality;

b) a co-anion;
c) a nucleophilic substituent, optionally in salt form; and
d) a polar solvent, where the polar solvent is present in an amount such that the ratio by mass between the sum of the polar solvents and the sum of the phosphonium salts ([S.P.]/[P+1]), i.e. [S.P.]/(a+b), is not more than 1, and the sum of (a)+(b)+(c)+(d) represents 100% of said liquid phase; and where the molar ratio between the phosphonium compound and the substrate at the start of said reaction is at least 2/3.

2. The process of claim 1, wherein the co-anion is an anion selected from the group consisting of halides and mixtures thereof.

3. The process of claim 1, further comprising an anionic nucleophile for which the pKa of the associated acid is not more than 5.

4. The process of claim 1, comprising fluoride ions.

5. The process of claim 1, wherein the sum of the bromide and the chloride ions is at least equal to 1/2 the amount of cation of formula I' (expressed as equivalents).

6. The process of claim 1, having a ratio by mass between the water and the salt whose cation corresponds to the formula I' of not more than 200 ppm.

7. The process of claim 1, excluding substrate, having a ratio by mass between component (d) and components (a)+(b)+(c) being not more than 1.

8. The process of claim 1, having, when the nucleophile is ionic, a molar ratio between component (c) and component (a) greater than 0.01.

9. The process of claim 1, having, when the nucleophile is ionic, at least part of the co-anion formed from said nucleophile.

10. The process of claim 1, having, when the nucleophile is ionic, a ratio (or equivalents ratio when the components are polyfunctional) between component (c) and component (a) greater than 0.5.

11. The process of claim 1, further comprising a solid phase.

12. The process of claim 1, wherein said solid phase comprises at least one salt formed from a mineral cation and the anion corresponding to said nucleophile or from the leaving group of said nucleophilic substitution.

13. The process of claim 1, having said nucleophilic substituent present in the liquid phase in the form of a salt with a mineral cation and a molar ratio (or equivalents ratio) between said dissolved mineral cation and component (a) (MC/[P$^{+1}$]) of at least 1/100.

14. The process of claim 13, wherein said nucleophile is the fluoride ion in the form of an alkali metal salt.

15. The process of claim 1, wherein the anion or anion mixture which ensures electroneutrality is at most as nucleophilic as the nucleophile.

16. The process of claim 1, wherein the anion or anion mixture which ensures electroneutrality is at least as acidic as acetic acid.

17. The process of claim 1, wherein the anion or anion mixture which ensures electroneutrality is a halogen.

18. The process of claim 1, wherein the group Ar further comprises at least one leaving group other than Ξ, wherein said at least one leaving group other than Ξ is selected from the group consisting of halogens, pseudo halogens and a nitro group and said at least one leaving group other than Ξ is identical to or different from Ξ.

19. The process of claim 1, wherein the sum of the $\sigma_p$ (Hammett constants) of the substituents Ar, apart from Ξ, is not more than 1.

20. The process of claim 1, wherein Ar is such that the aromatic nucleus carrying Ξ is a 6-membered nucleus whose electron-withdrawing groups are groups which withdraw electrons by inductive and not mesomeric effect.

21. The process of claim 20, wherein Ar is such that the aromatic nucleus carrying Ξ is a 6-membered nucleus whose electron-withdrawing groups are halogens.

22. The process of claim 21, wherein Ar is such that the aromatic nucleus carrying Ξ is a 6-membered nucleus of which the electron-withdrawing group or at least one of the electron-withdrawing groups is positioned meta to Ξ, and is a chlorine or a fluorine.

23. The process of claim 20, wherein Ξ is a group whose departure leads to an oxygenated anion, whose anionic charge being carried by a chalcogen atom, and whose acidity, expressed in terms of the Hammett constant, is at least equal to that of acetic acid, a chlorine or a bromine.

24. The process of claim 1, wherein the nucleophile is a fluoride ion.

25. The process of claim 24, wherein the substrate is 1,3,5-trichlorobenzene, 1,3-dichloro, 5-fluorobenzene or 1-chloro, 3,5-difluorobenzene.

26. The process of claim 1, wherein said phosphonium compound is Bu$_4$PBr.

27. The process according to claim 1, wherein the group Ar further comprises at least one group having a withdrawing effect selected from the group consisting of a halogen atom, NO$_2$, SO$_2$Alk, SO$_3$Alk, a perfluoroAlk, CF$_3$, CN, CHO, COAlk, COΞ', COOAlk, a phosphonyl and a phosphonate, where Ξ' is as defined in claim 1, and the symbol Alk representing a hydrogen atom or a linear or branched alkyl group.

28. The process according to claim 1, wherein the molar ratio between the phosphonium compound and the substrate is at least 2/3 and the polar solvent is aprotic and the ratio by mass between the sum of the polar solvents and the sum of the phosphonium salts ([S.P.]/[P+]), i.e. [S.P.]/(a+b), is not more than 1/5.

29. The process according to claim 1, wherein the R$_1$, R$_2$, R$_3$, and R$_4$, radicals have a total carbon number is not more than 50.

30. The process according to claim 29, wherein the total carbon number is not more than 25.

31. The process according to claim 1, wherein the $R_1$, $R_2$, $R_3$, and $R_4$, comprise at least three aliphatic hydrocarbon radicals, whose total carbon number is not more than 25.

32. The process according to claim 1, wherein said nucleophilic substitution is being conducted at a temperature ranging from 150 to 250° C.

33. The process according to claim 27, wherein the symbol Alk representing a hydrogen atom or a linear or branched alkyl group comprising 1 to 4 carbons.

* * * * *